(12) United States Patent
Squitieri et al.

(10) Patent No.: US 11,737,905 B2
(45) Date of Patent: Aug. 29, 2023

(54) INFLATABLE PERFUSION ENHANCEMENT APPARATUSES AND ASSOCIATED DEVICES, SYSTEMS AND METHODS

(71) Applicant: TurnCare, Inc., Palo Alto, CA (US)

(72) Inventors: Rafael Paolo Squitieri, Wilton, CT (US); Robert Charles Deutsch, Oakridge, NJ (US); Steven Bruce Frazier, Sloatsburg, NY (US); Robert Loiacono, Young Harris, GA (US); Linda Seaman, Bridgeport, CT (US); Erica Kelly, Bridgeport, CT (US)

(73) Assignee: TurnCare, Inc., Palo Alto, CA (US)

( * ) Notice: Subject to any disclaimer, the term of this patent is extended or adjusted under 35 U.S.C. 154(b) by 2 days.

(21) Appl. No.: 17/495,072

(22) Filed: Oct. 6, 2021

(65) Prior Publication Data
US 2022/0023087 A1    Jan. 27, 2022

Related U.S. Application Data

(62) Division of application No. 16/363,094, filed on Mar. 25, 2019.
(Continued)

(51) Int. Cl.
*A61F 5/34*    (2006.01)
*A61L 31/10*    (2006.01)
(Continued)

(52) U.S. Cl.
CPC .............. *A61F 5/34* (2013.01); *A61F 5/32* (2013.01); *A61L 31/10* (2013.01); *A61L 31/14* (2013.01); *B29D 22/02* (2013.01); *A61L 2420/02* (2013.01)

(58) Field of Classification Search
CPC ...... A61F 5/34; A61F 5/0193; A61F 5/05816; A61F 13/51474; A61F 7/00;
(Continued)

(56) References Cited

U.S. PATENT DOCUMENTS 4,175,297 A   11/1979   Richardson et al.
4,967,756 A   11/1990   Hewitt
(Continued)

FOREIGN PATENT DOCUMENTS

CN    2774770 Y    4/2006
CN    104363873 A    2/2015
(Continued)

OTHER PUBLICATIONS

International Search Report and Written Opinion dated Feb. 4, 2020 for International Application No. PCT/US19/53246, 13 pages.

*Primary Examiner* — Dah-Wei D. Yuan
*Assistant Examiner* — Andrew J Bowman
(74) *Attorney, Agent, or Firm* — Perkins Coie LLP; Andrew T. Pettit

(57) ABSTRACT

Introduced here are pressure-mitigation apparatuses for mitigating the pressure applied to a human body by the support surface of an object. The pressure-mitigation apparatus can include a series of chambers that can be individually controlled to vary the pressure therein. By varying the chamber pressure, the main point of pressure applied by the support surface to the human body may be moved across the surface of the human body. An attachment apparatus may be used to securely adhere the pressure-mitigation apparatus to the support surface.

13 Claims, 17 Drawing Sheets

Related U.S. Application Data

(60) Provisional application No. 62/736,758, filed on Sep. 26, 2018, provisional application No. 62/690,206, filed on Jun. 26, 2018, provisional application No. 62/647,551, filed on Mar. 23, 2018.

(51) Int. Cl.
*A61F 5/32* (2006.01)
*B29D 22/02* (2006.01)
*A61L 31/14* (2006.01)

(58) Field of Classification Search
CPC ... A47C 27/083; A61H 9/0078; F16K 31/004; A61G 7/0527
See application file for complete search history.

(56) References Cited

U.S. PATENT DOCUMENTS

| | | | |
|---|---|---|---|
| 5,461,741 | A | 10/1995 | Graebe |
| 5,840,050 | A * | 11/1998 | Lerman ............... A61F 5/0193 602/19 |
| 6,237,598 | B1 | 5/2001 | Sereboff |
| 6,901,617 | B2 | 6/2005 | Sprouse et al. |
| 7,188,620 | B2 | 3/2007 | Amarasinghe |
| 9,901,491 | B2 | 2/2018 | Squitieri |
| 2002/0104165 | A1 | 8/2002 | Gross |
| 2004/0034936 | A1 | 2/2004 | Welling et al. |
| 2004/0048062 | A1 * | 3/2004 | Nonaka ................ C09J 11/08 428/354 |
| 2004/0206409 | A1 | 10/2004 | Yano et al. |
| 2006/0149176 | A1 | 7/2006 | Bolam et al. |
| 2007/0118993 | A1 | 5/2007 | Bates |
| 2008/0201853 | A1 | 8/2008 | Graebe |
| 2008/0287037 | A1 | 11/2008 | Solberg |
| 2010/0042026 | A1 | 2/2010 | Kloecker et al. |
| 2011/0185508 | A1 | 8/2011 | Hsu et al. |
| 2012/0304384 | A1 * | 12/2012 | Scholz ................ A61F 7/00 5/81.1 R |
| 2013/0219626 | A1 | 8/2013 | Clapper |
| 2013/0255699 | A1 | 10/2013 | Squitieri |
| 2014/0059781 | A1 | 3/2014 | Laflèche et al. |
| 2015/0164677 | A1 | 6/2015 | Squitieri |
| 2015/0224005 | A1 | 8/2015 | Kramer et al. |
| 2015/0238378 | A1 | 8/2015 | Bhat et al. |
| 2016/0193090 | A1 * | 7/2016 | Squitieri .......... A61F 13/51474 128/889 |
| 2016/0317370 | A1 | 11/2016 | Evans et al. |
| 2019/0021918 | A1 | 1/2019 | Squitieri |

FOREIGN PATENT DOCUMENTS

| | | |
|---|---|---|
| CN | 205181608 U | 4/2016 |
| CN | 105980501 A | 9/2016 |
| CN | 107427404 A | 12/2017 |
| CN | 107429130 A | 12/2017 |
| EP | 2250988 A2 | 11/2010 |
| JP | H01202433 A | 8/1989 |
| JP | 2010051596 A | 3/2010 |
| WO | 2005082314 A1 | 9/2005 |

* cited by examiner

500

501
Acquire a first sheet comprised of a first material

502
Acquire a second sheet comprised of a second material

503
Create a cavity by forming an interconnection along the periphery of the first and second sheets

504
Create a geometric pattern of chambers by forming additional interconnections between the first and second sheets

505
Apply a coating to the exterior surface of the first sheet and/or the second sheet

1201
Acquire a pressure-mitigation apparatus to be placed between a human body and a support surface 1202
Acquire an attachment apparatus associated with the pressure-mitigation apparatus and/or the support surface 1203
Secure the attachment apparatus to the support surface 1204
Secure the pressure-mitigation apparatus to the attachment apparatus 1205
Connect the pressure-mitigation apparatus to a controller 1206
Arrange the human body over the pressure-mitigation apparatus 1207
Cause chambers of the pressure-mitigation apparatus to be inflated in accordance with a pattern

FIGURE 12

INFLATABLE PERFUSION ENHANCEMENT APPARATUSES AND ASSOCIATED DEVICES, SYSTEMS AND METHODS

CROSS-REFERENCE TO RELATED APPLICATIONS

This application is a divisional of U.S. patent application Ser. No. 16/363,094, filed Mar. 25, 2019, which claims benefit of and priority to U.S. Provisional Patent Application No. 62/647,551, filed on Mar. 23, 2018, U.S. Provisional Patent Application No. 62/690,206, filed on Jun. 26, 2018, and U.S. Provisional Patent Application No. 62/736,758, filed on Sep. 26, 2018, all of which are incorporated herein by reference in their entireties.

TECHNICAL FIELD

The present technology relates generally to apparatuses, systems, and methods for enhancing perfusion and mitigating the contact pressure applied to a human body by a support surface.

BACKGROUND

Pressure injuries (sometimes referred to as "decubitus ulcers," "pressure ulcers," "pressure sores," or "bedsores") typically occur as a result of steady pressure applied in one location along a surface of the human body such as, for example, the sacrum. Pressure injuries are most common in individuals who are mobility-impaired or immobilized (e.g., in a wheelchair or a bed, or on an operating table) for prolonged periods of time. Oftentimes these individuals are older, malnourished, and/or incontinent, all factors that predispose the human body to pressure injury formation. Because these individuals are often not ambulatory, they may sit or lie for prolonged periods of time in the same position. Moreover, these individuals often are unable to reposition themselves to alleviate the pressure. Consequently, the pressure on the skin and soft tissue eventually causes ischemia or inadequate blood flow to the area, thereby resulting in breakdown of the skin and tissue damage. Pressure injuries can result in a superficial injury to the skin, or a deeper full-thickness ulcer that exposes underlying tissues and places the individual at risk for infection. The resulting infection may worsen, leading to sepsis, or even death in some cases.

There are various pressure technologies on the market for preventing pressure injuries. However, conventional alternating-pressure technologies have many deficiencies, including the inability to control the spatial relationship between an individual and a support surface. Consequently, individuals using conventional alternating-pressure technologies may still develop pressure injuries or suffer from related complications.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. Furthermore, components may be shown as transparent in certain views for the purpose of illustration, rather than to indicate that the component is necessarily transparent. Any headings provided herein are for convenience only.

FIG. 5 is a flow diagram of a process for manufacturing a pressure-mitigation apparatus in accordance with embodiments of the present technology.

FIG. 12 is a flow diagram of a process for deploying a pressure-mitigation system designed to prevent and/or address ischemia-reperfusion injuries in accordance with embodiments of the present technology.

DETAILED DESCRIPTION

Figure 1A:
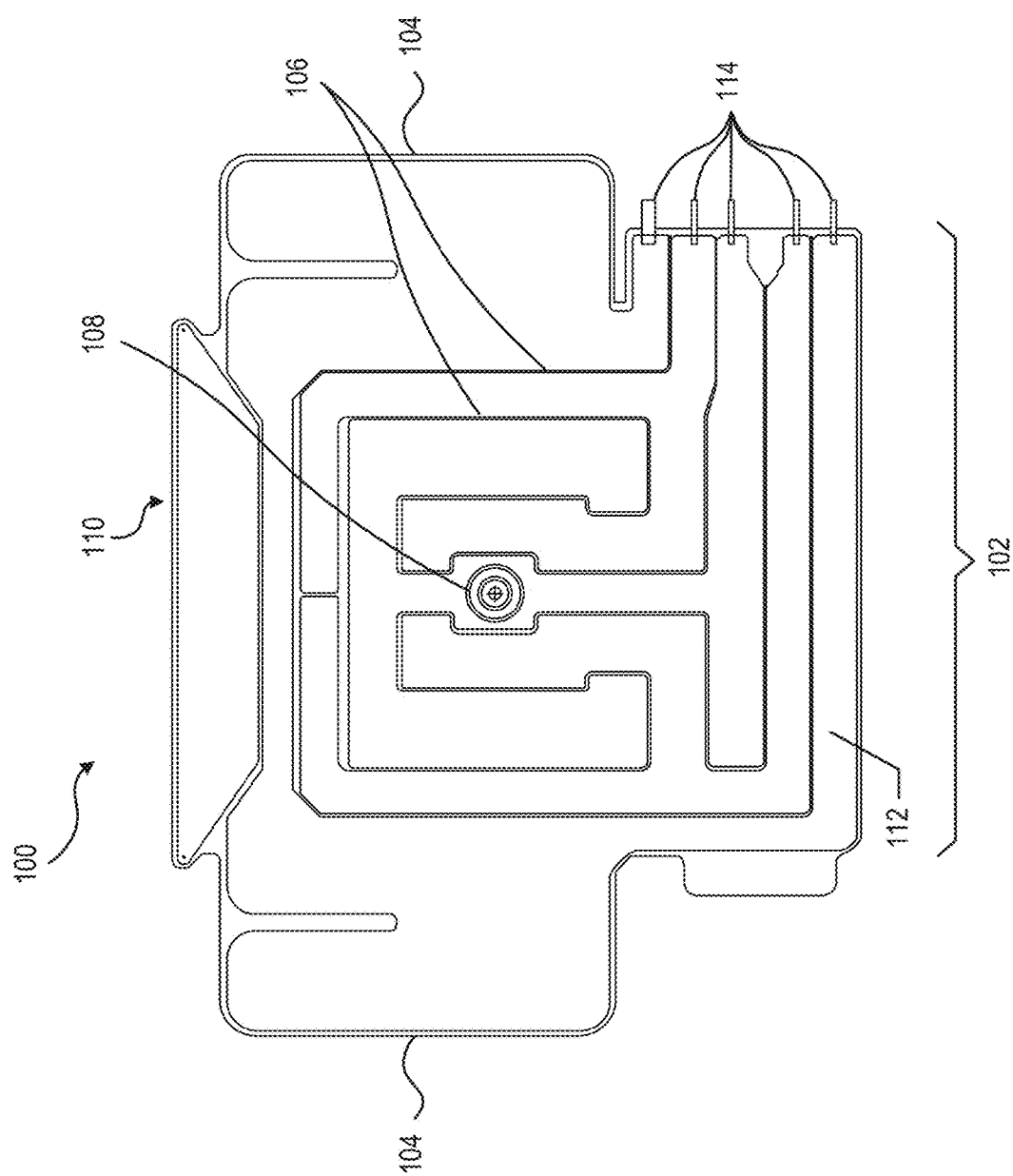
FIGS. 1A and 1B are top and bottom views, respectively, of a pressure-mitigation apparatus configured in accordance with embodiments of the present technology.

Pressure injuries (also referred to a "pressure ulcers" or "ulcers") are localized regions of damage to the skin and/or the underlying tissue that result from contact pressure (or simply "pressure") on the corresponding anatomical region of the body. Pressure injuries often form over bony prominences, such as the skin and soft tissue overlying the sacrum, coccyx, heels, or hips. However, other sites (e.g., the elbows, knees, ankles, shoulders, abdomen, back, or cranium) may also be affected. Generally, pressure injuries develop when pressure is applied to blood vessels in soft tissue, which at least partially obstructs blood flow to the soft tissue (e.g., when the pressure exceeds the capillary filling pressure) and causes ischemia at the pressure site for an extended duration. Therefore, pressure injuries often occur in individuals who are mobility-impaired, immobilized, or sedentary for prolonged periods of times. Once a pressure injury forms, the healing process is typically slow. For example, when pressure is relieved from the site of the pressure injury, the body rushes blood (including proinflammatory mediators) to that region to perfuse the area. The sudden reperfusion of the damaged, previously ischemic region has been shown to cause an inflammatory response, brought on by the proinflammatory mediators, that can actually worsen the original pressure injury and prolong recovery. Further, depending on the patient and the pressure injury, the proinflammatory mediators may spread through the blood stream beyond the site of the pressure injury to cause a systematic inflammatory response. This secondary inflammatory response caused by the proinflammatory mediators has been shown to exacerbate existing conditions or trigger additional ailments, thereby slowing recovery. Moreover, recovery time can be prolonged by numerous factors often associated with individuals prone to pressure injuries, such as old age, immobility, preexisting medical conditions (e.g., arteriosclerosis, diabetes, or infection), smoking, and/or medications (e.g., anti-inflammatory drugs). Thus, preventing or reducing pressure injury formation (and reducing proinflammatory mediators) can enhance and expedite many treatment processes for individuals, especially those who experience impaired mobility during the course of treatment.

Introduced here, therefore, are inflatable perfusion enhancement apparatuses for mitigating the pressure applied to a human body by the support surface of an object. The inflatable perfusion enhancement apparatus (also referred to as a "pressure-mitigation apparatus," a "pressure-mitigation device," or a "pressure-mitigation pad") can include a series of chambers (also referred to as "cells") whose pressure can be individually varied. By varying the pressure in the series of chambers, the main point of pressure applied by the support surface to the human body may be moved across the surface of the human body. For example, following deployment of the pressure-mitigation apparatus, the main point of pressure may be moved amongst a plurality of predetermined locations by sequentially varying the pressure in different predetermined subjects of chambers. The support surface (also referred to as a "contact surface") may be the surface of a chair, a mattress, a stretcher, an operating table, or some other physical object on which the individual places his or her weight.

A pressure-mitigation apparatus can include a first layer designed to face the support surface and a second layer designed to face the human body supported by the support surface. The series of chambers may be formed via interconnections between the first and second layers (e.g., either directly or via one or more intermediary layers), and each chamber may be independently pressurized via a discrete airflow.

Pressure-mitigation apparatuses may be designed based on the expected physical orientation of the human body during use. For example, some pressure-mitigation apparatuses have geometric arrangements of chambers suitable for the dorsal side of the human body in a sitting position, while other pressure-mitigation apparatuses have geometric arrangements of chambers suitable for the dorsal side of the human body in a supine and/or prone position. Moreover, a pressure-mitigation apparatus may be designed based on one or more characteristics of the individual(s) who are expected to use the pressure-mitigation apparatus, such as size, weight, or physical ailment. For example, different pressure-mitigation apparatuses may be available for neonatal patients, pediatric patients, average adult patients, bariatric patients, or geriatric patients.

As further described below, a pressure-mitigation apparatus may be part of a pressure-mitigation system that also includes an attachment apparatus, a controller device (also referred to as a "controller"), and one or more pumps. The attachment apparatus can ensure the pressure-mitigation apparatus is securely adhered to the support surface. The controller, meanwhile, can cause the pressure on one or more anatomical regions of the human body to be varied by controlling the flow of fluid (e.g., air) produced by the pump(s) into each chamber of the pressure-mitigation apparatus. For example, the controller may controllably inflate one or more chambers, deflate one or more chambers, or any combination thereof.

Specific details of several embodiments of the present technology are described herein with reference to FIGS. 1-13. Although many of the embodiments are described herein with respect to systems, apparatuses, and methods for alleviating the pressure applied to a human body (e.g., a patient, individual, or subject) in a certain position (e.g., the supine position) by a certain support surface (e.g., a mattress), other embodiments in addition to those described herein are within the scope of the present technology. For example, at least some embodiments of the present technology may be useful for alleviating the pressure applied to a human body in a sitting position. In such embodiments, the chambers of the pressure-mitigation apparatus may be different sizes, in different arrangements, and/or otherwise differ from the chambers of pressure-mitigation apparatuses for patients oriented in a supine position. Additionally or alternatively, the chambers of the pressure-mitigation apparatus may be inflated in a different order, with different pressures, for different durations, and/or otherwise have a different inflation pattern than those of pressure-mitigation apparatuses for patients oriented in a supine position.

It should be noted that other embodiments in addition to those disclosed herein are within the scope of the present technology. For example, components, configurations, and/or procedures shown or described with respect to one embodiment can be combined with or replace the components, configurations, and/or procedures described in other embodiments. Further, embodiments of the present technology can have different components, configurations, and/or procedures than those shown or described herein. Moreover, a person of ordinary skill in the art will understand that embodiments of the present technology can have configurations, components, and/or procedures in addition to those shown or described herein, and that these and other embodiments can be without several of the configurations, components, and/or procedures shown or described herein without deviating from the present technology.

Selected Embodiments of Pressure-Mitigation Apparatuses

A pressure-mitigation apparatus includes a plurality of chambers or compartments that can be individually controlled to vary the pressure in each chamber and/or a subset of the chambers. When placed between a human body and a support surface, the pressure-mitigation apparatus can vary the pressure on an anatomical region by controllably inflating one or more chambers, deflating one or more chambers, or any combination thereof. Several examples of pressure-mitigation apparatuses are described below with respect to FIGS. 1A-3. Unless otherwise noted, any features described with respect to one embodiment are equally applicable to the other embodiments. Some features have only been described with respect to a single embodiment of the pressure-mitigation apparatus for the purpose of simplifying the present disclosure.

Figure 1B:
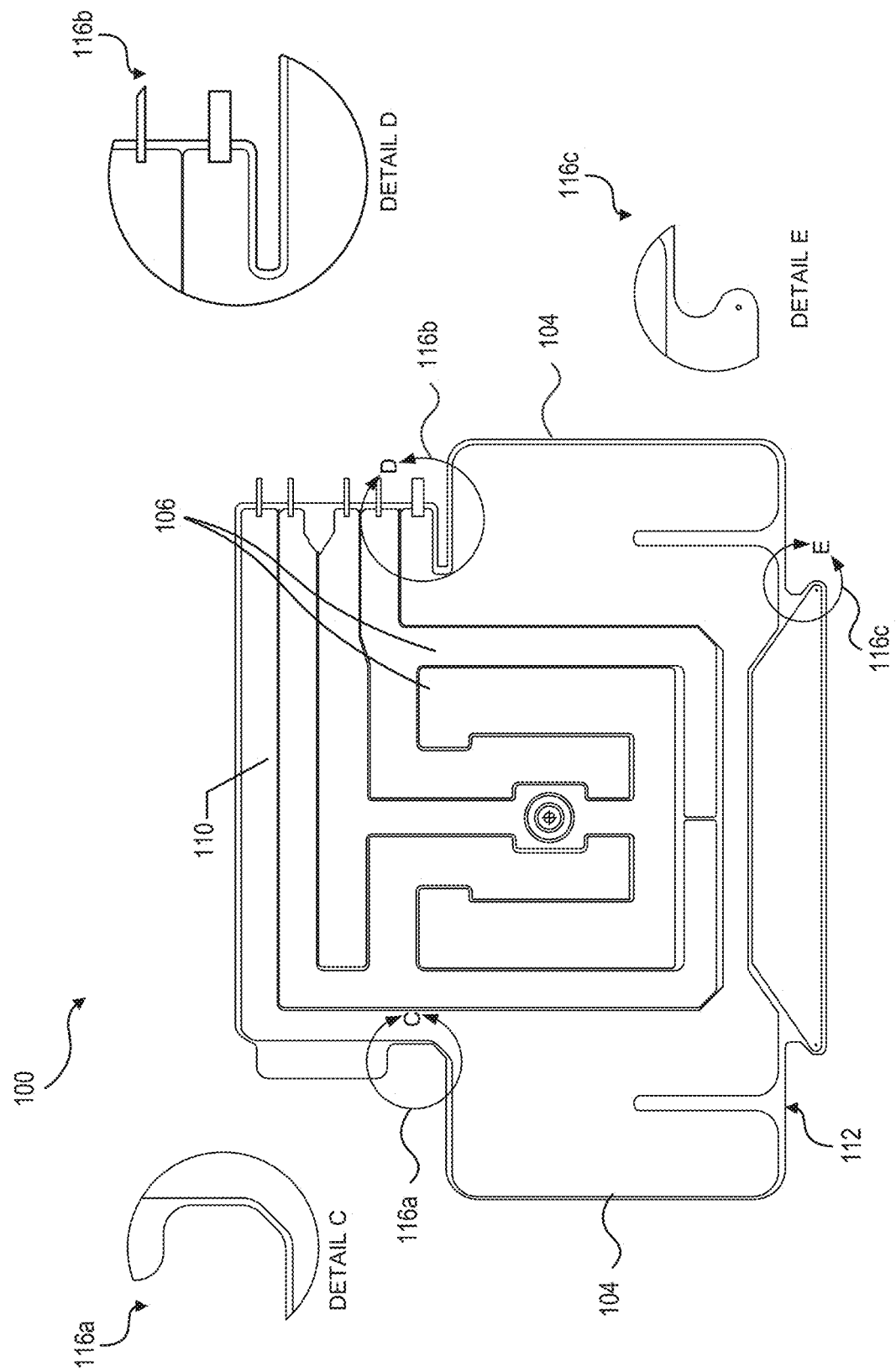

FIGS. 1A and 1B are top and bottom views, respectively, of a pressure-mitigation apparatus 100 for relieving pressure on a specific anatomical region applied by an elongated support surface in accordance with embodiments of the present technology. The pressure-mitigation apparatus 100 can be used in conjunction with elongated support surfaces, such as mattresses, stretchers, operating tables, and procedure tables. In some embodiments the pressure-mitigation apparatus 100 is secured to a support surface using an attachment apparatus, while in other embodiments the pressure-mitigation apparatus 100 is placed in direct contact with the support surface (i.e., without any attachment apparatus therebetween). Attachment apparatuses are further described below with respect to FIGS. 6-8.

As shown in FIG. 1A, the pressure-mitigation apparatus 100 can include a central portion 102 (also referred to as a "contact portion") positioned alongside at least one side support 104. Here, a pair of side supports 104 are arranged on opposing sides of the central portion 102. However, some embodiments of the pressure-mitigation apparatus 100 do not include any side supports. For example, the side support(s) 104 may be omitted when the individual is medically immobilized (e.g., under anesthesia, in a medically induced coma, etc.) and/or physically restrained by the underlying support surface (e.g., by rails along the side of a bed, armrests along the side of a chair) and/or other structures (e.g., physical restraints holding down the patient, casts, etc.).

The pressure-mitigation apparatus 100 includes a series of chambers 106 (also referred to as "cells") whose pressure can be individually varied. In some embodiments, the series of chambers 106 are arranged in a geometric pattern designed to relieve pressure on one or more specific anatomical regions of a human body. As noted above, when placed between the human body and a support surface, the pressure-mitigation apparatus 100 can vary the pressure on the specific anatomical region(s) by controllably inflating chamber(s), deflating chamber(s), or any combination thereof.

In some embodiments, the geometric pattern is designed to mitigate pressure on a specific anatomical region when the specific anatomical region is oriented over a target region 108 of the geometric pattern. As shown in FIGS. 1A and 1B, the target region 108 may represent a central point or portion of the pressure-mitigation apparatus 100 to appropriately position the person's anatomy with respect to the pressure-mitigation apparatus 100. For example, the target region 108 may correspond to an epicenter of the geometric pattern. However, the target region 108 may not necessarily be the central point of the pressure-mitigation apparatus 100, particularly if the pressure-mitigation apparatus 100 is not symmetric. The target region 108 may be marked so that an individual (e.g., a physician, nurse, caregiver, or the patient himself or herself) can readily align the target region 108 with a corresponding anatomical region of the human body to be positioned thereon.

The pressure-mitigation apparatus 100 can include a first portion 110 (also referred to as a "first layer" or a "bottom layer") designed to face a support surface and a second portion 112 (also referred to as a "second layer" or a "top layer") designed to face the human body supported by the support surface. In some embodiments the first portion 110 is directly adjacent to the support surface, while in other embodiments the first portion 110 is directly adjacent to an attachment apparatus designed to help secure the pressure-mitigation apparatus 100 to the support surface. The pressure-mitigation apparatus 100 may be constructed of a variety of materials, and the material(s) used in the construction of each component of the pressure-mitigation apparatus 100 may be chosen based on the nature of the body contact, if any, to be experienced by the component. For example, because the second portion 112 will often be in direct contact with the skin, it may be comprised of a soft fabric or a breathable fabric (e.g., comprised of moisture-wicking materials or quick-drying materials, or having perforations). In some embodiments, an impervious lining (e.g., comprised of polyurethane) is secured to the inside of the second portion 112 to inhibit fluid (e.g., sweat) from entering the series of chambers 106. As another example, if the pressure-mitigation apparatus 100 is designed for deployment beneath a cover (e.g., a bed sheet), then the second portion 112 may be comprised of a liquid-impervious, flexible material, such as polyurethane, polypropylene, silicone, or a rubber compound. The first portion 110 may also be comprised of a liquid-impervious, flexible material.

The series of chambers 106 may be formed via interconnections between the first and second portions 110, 112 (e.g., either directly or via one or more intermediary layers). In the embodiment illustrated in FIGS. 1A and 1B, the pressure-mitigation apparatus 100 includes an "M-shaped" chamber intertwined with two "C-shaped" chambers that face one another. Such an arrangement has been shown to effectively mitigate the pressure applied to the sacral region of a human body in the supine position by a support surface when the pressure in these chambers is alternated. A pressure-mitigation apparatus may have another arrangement of chambers if the pressure-mitigation apparatus is designed for an anatomical region other than the sacral region, or if the pressure-mitigation apparatus is to be used to support a human body in a non-supine position (e.g., a sitting position). Generally, the geometric pattern of the chambers 106 is designed based on the internal anatomy (e.g., the muscles, bones, and vasculature) of a specific anatomical region on which pressure is to be relieved.

The person using the pressure-mitigation apparatus 100 and/or the caregiver (e.g., a nurse, physician, etc.) will often be responsible for actively orienting the anatomical region of the patient lengthwise over the target region 108 of the geometric pattern. However, the side support(s) 104 may actively orient or guide the specific anatomical region of the human body laterally over the target region 108 of the geometric pattern. In some embodiments the side support(s) 104 are inflatable, while in other embodiments the side support(s) 104 are permanent structures that protrude from one or both lateral sides of the pressure-mitigation device 100. For example, at least a portion of each side support may be stuffed with cotton, latex, polyurethane foam, or any combination thereof.

A controller (not shown) can separately control the pressure in each chamber (as well as the side supports 104, if included) by providing a discrete airflow via one or more corresponding valves 114. Such a controller is described in further detail with respect to FIGS. 10A-11 In some embodiments, the valves 114 are permanently secured to the pressure-mitigation apparatus 100 and designed to interface with tubing that can be readily detached (e.g., for easier transport, storage, etc.). Here, the pressure-mitigation apparatus 100 includes five valves 114. Three valves are fluidly coupled to the series of chambers 106, and two valves are fluidly coupled to the side supports 104. In other embodiments, the pressure-mitigation apparatus 100 includes more than five valves 114 and/or less than five valves 114.

In some embodiments, the pressure-mitigation apparatus 100 includes one or more structural feature(s) 116a-c that enhance securement of the pressure-mitigation apparatus 100 to a support surface and/or an attachment apparatus. As illustrated in FIG. 1B, for example, the pressure-mitigation apparatus 100 can include three design feature(s) 116a-c, each of which can be aligned with a corresponding structural feature that is accessible along the support surface or the attachment apparatus. For example, each design feature 116a-c may be designed to at least partially envelope a structural feature that protrudes upward. The design feature(s) 116a-c may also facilitate proper alignment of the pressure-mitigation apparatus 100 with the support surface or the attachment apparatus.

Figure 2A:
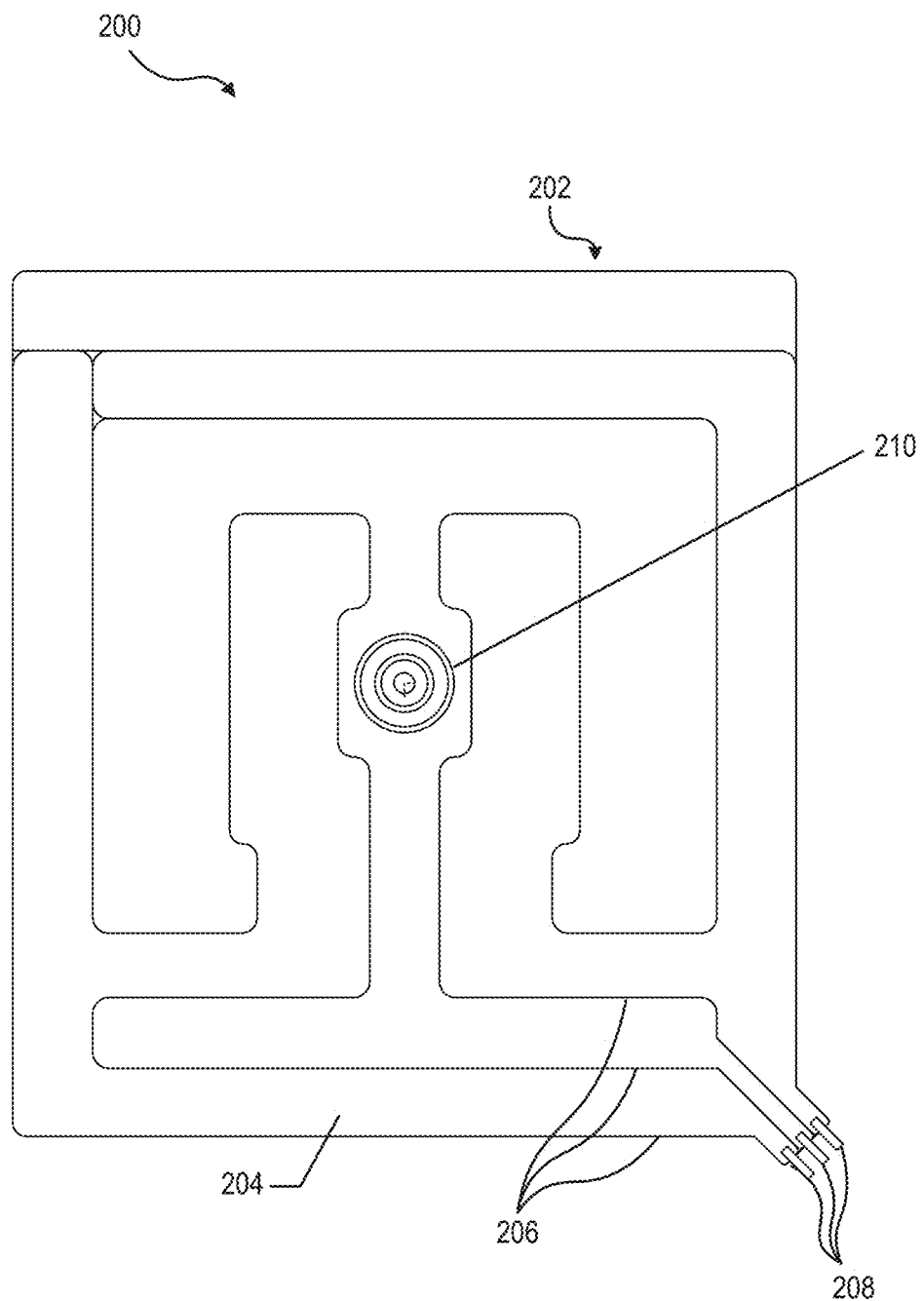
FIGS. 2A and 2B are top and bottom views of a pressure-mitigation apparatus configured in accordance with embodiments of the present technology.
Figure 2B:
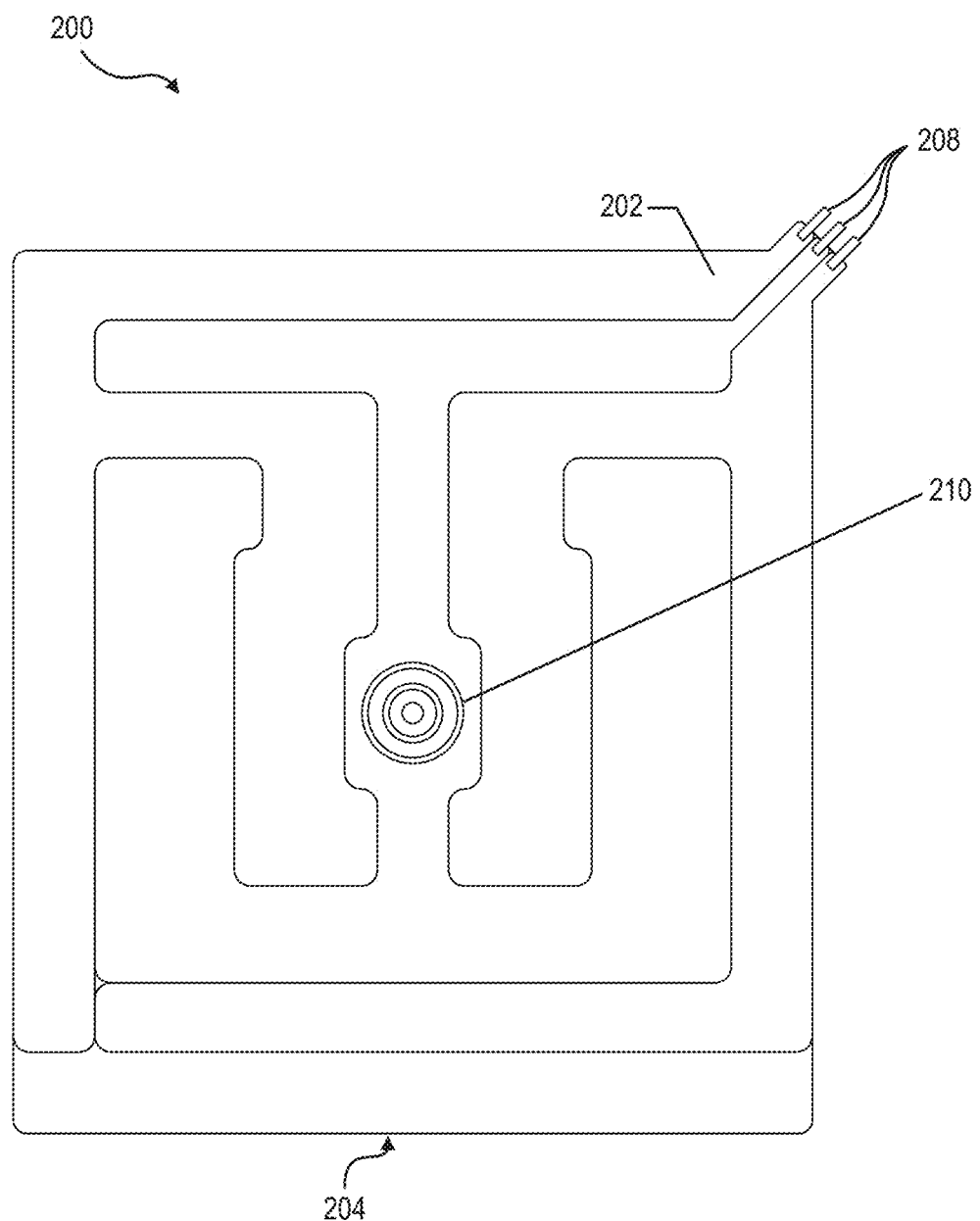

FIGS. 2A and 2B are top and bottom views, respectively, of a pressure-mitigation apparatus 200 for relieving pressure on a specific anatomical region applied by a support surface in accordance with embodiments of the present technology. The pressure-mitigation apparatus 200 can be used in conjunction with nonelongated support surfaces that support individuals in a seated or partially erect position, such as chairs (e.g., office chairs, examination chairs, recliners, and wheelchairs) and the seats included in vehicles and airplanes. As such, the pressure-mitigation apparatus 200 will often be positioned atop support surfaces that have side supports integrated into the support itself (e.g., the side arms of a recliner or wheelchair). In some embodiments the pressure-mitigation apparatus 200 is secured to a support surface using an attachment apparatus, while in other embodiments the attachment apparatus is omitted such that the pressure-mitigation apparatus 200 directly contacts the underlying support surface.

The pressure-mitigation apparatus 200 can include various features generally similar to the features of the pressure-mitigation device 100 described above with respect to FIGS. 1A and 1B. For example, the pressure-mitigation apparatus 200 may include a first portion 202 (also referred to as a "first layer" or a "bottom layer") designed to face the support surface, a second portion 204 (also referred to as a "second layer" or a "top layer") designed to face the human body supported by the support surface, and a plurality of chambers 206 formed via interconnections between the first and second portions 202, 204. In this embodiment, the pressure-mitigation apparatus 200 includes an "M-shaped" chamber 206 intertwined with a backward "J-shaped" chamber 206 and a backward "C-shaped" chamber 206. The alternating inflation/deflation of such an arrangement of chambers 206 has been shown to effectively mitigate the pressure applied by a support surface to the sacral region when the human body is in a seated position.

The individual inflation/deflation of these chambers 206 can be performed in a predetermined pattern and to predetermined pressure levels. In some embodiments, for example, the individual chambers 206 can be inflated to higher pressure levels than the chambers 206 of the pressure-mitigation apparatus 100 described with respect to FIGS. 1A and 1B because the human body supported by the pressure-mitigation apparatus 200 is in a seated position, thereby applying more pressure on the pressure-mitigation apparatus 200 than if the human body were supine or prone. Further, unlike the pressure mitigation device 100 of FIGS. 1A and 1B, the pressure-mitigation apparatus 200 of FIGS. 2A and 2B does not include side supports. As noted above, side supports may be omitted when the structure on which the individual is seated or reclined already provides components that laterally center the individual (e.g., rails along the side of a bed, armrests along the side of a chair), as is often the case with nonelongated support surfaces.

As further described below with respect to FIGS. 10A-11, a controller can control the pressure in each chamber 206 by providing a discrete airflow via one or more corresponding valves 208. Here, the pressure-mitigation apparatus 200 includes three valves 208, and each of the three valves 208 corresponds to a single chamber 206. In other embodiments, the pressure-mitigation apparatus 200 may include one valve, two valves, or more than three valves, and each valve can be associated with a specific chamber for individually controlled inflation and/or deflation of that chamber. In these and other embodiments, a single valve 208 can be fluidly coupled to two or more chambers 206. In these and other embodiments, a single chamber 206 can be in fluid communication with two or more valves 208 (e.g., one valve for inflation and another valve for deflation).

Similar to the pressure-mitigation apparatus 100 described with respect to FIGS. 1A and 1B, the pressure-mitigation apparatus 200 of FIGS. 2A and 2B includes a target region 210 over which a specific anatomical region can be positioned. Generally, the chambers 206 are arranged in a geometric pattern that is designed to mitigate pressure on the specific anatomical region. In some embodiments, the target region 210 represents a central point or portion of the pressure-mitigation apparatus 200. However, as shown in FIGS. 2A and 2B, the geometric pattern of chambers 206 may not be symmetric with respect to the x-axis or y-axis that extend through the target region 210.

Figure 3:
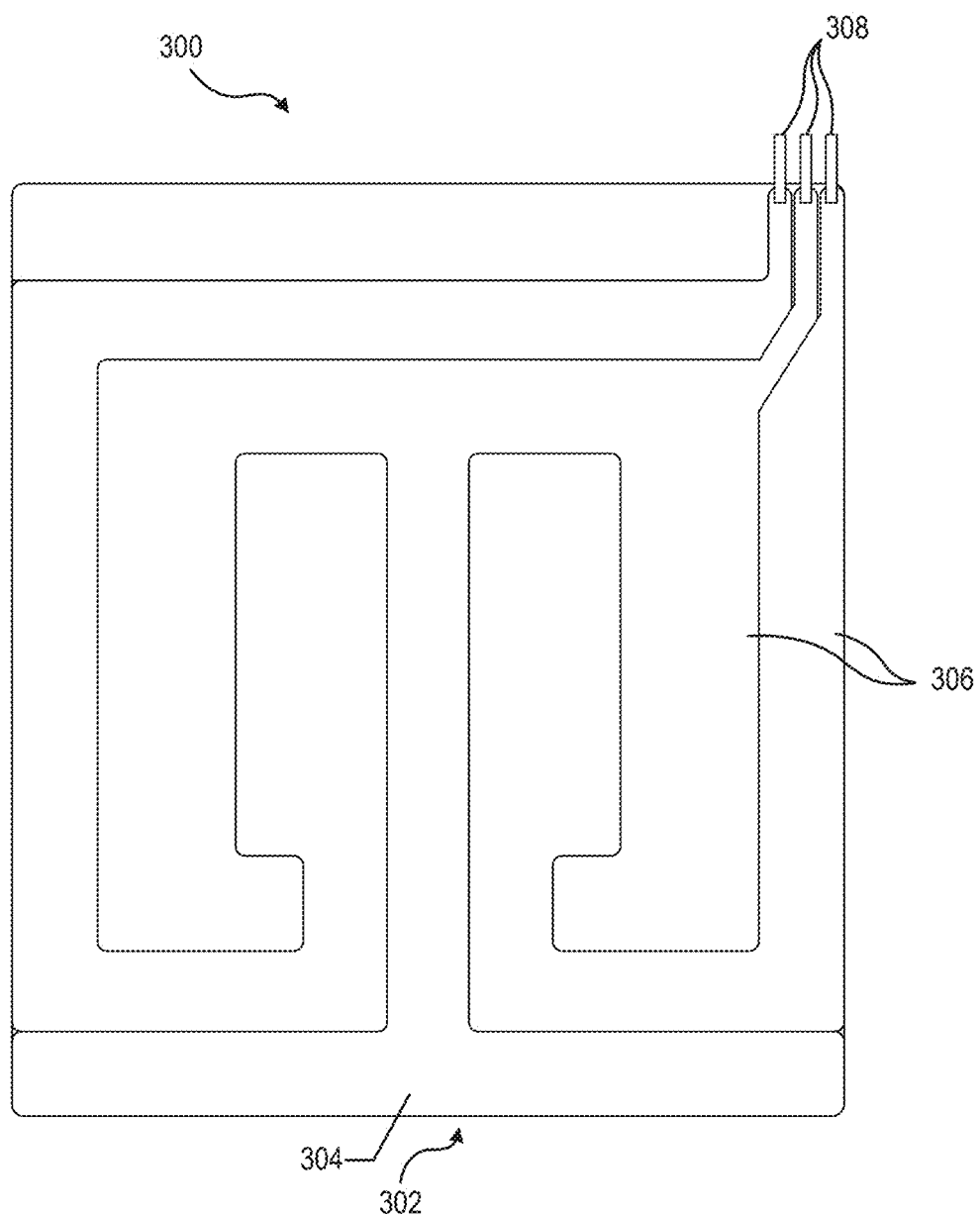
FIG. 3 is a top view of a pressure-mitigation apparatus configured in accordance with embodiments of the present technology.

FIG. 3 is a top view of a pressure-mitigation apparatus 300 for relieving pressure on a specific anatomical region applied by a wheelchair in accordance with embodiments of the present technology. The pressure-mitigation apparatus 300 can include various features generally similar to the features of the pressure-mitigation apparatus 200 of FIGS. 2A and 2B and the pressure-mitigation apparatus 100 of FIGS. 1A and 1B described above. For example, the pressure-mitigation apparatus 300 can include a first portion 302 (also referred to as a "first layer" or a "bottom layer") designed to face the seat of the wheelchair (i.e., the support surface), a second portion 304 (also referred to as a "second layer" or a "top layer") designed to face the human body supported by the seat of the wheelchair, a plurality of chambers 306 formed by interconnections between the first and second portions 302, 304, and a plurality of valves 308 that control the flow of fluid into and/or out of the chambers 306. In some embodiments the first portion 302 is directly adjacent to the seat of the wheelchair, while in other embodiments the first portion 302 is directly adjacent to an attachment apparatus. As shown in FIG. 3, the pressure-mitigation apparatus 300 may include an "M-shaped" chamber 306 intertwined with a "U-shaped" chamber 306 and a "C-shaped" chamber 306, which are inflated and deflated in accordance with a predetermined pattern to mitigate the pressure applied to the sacral region of a human body in a sitting position on the seat of a wheelchair.

Figure 4:
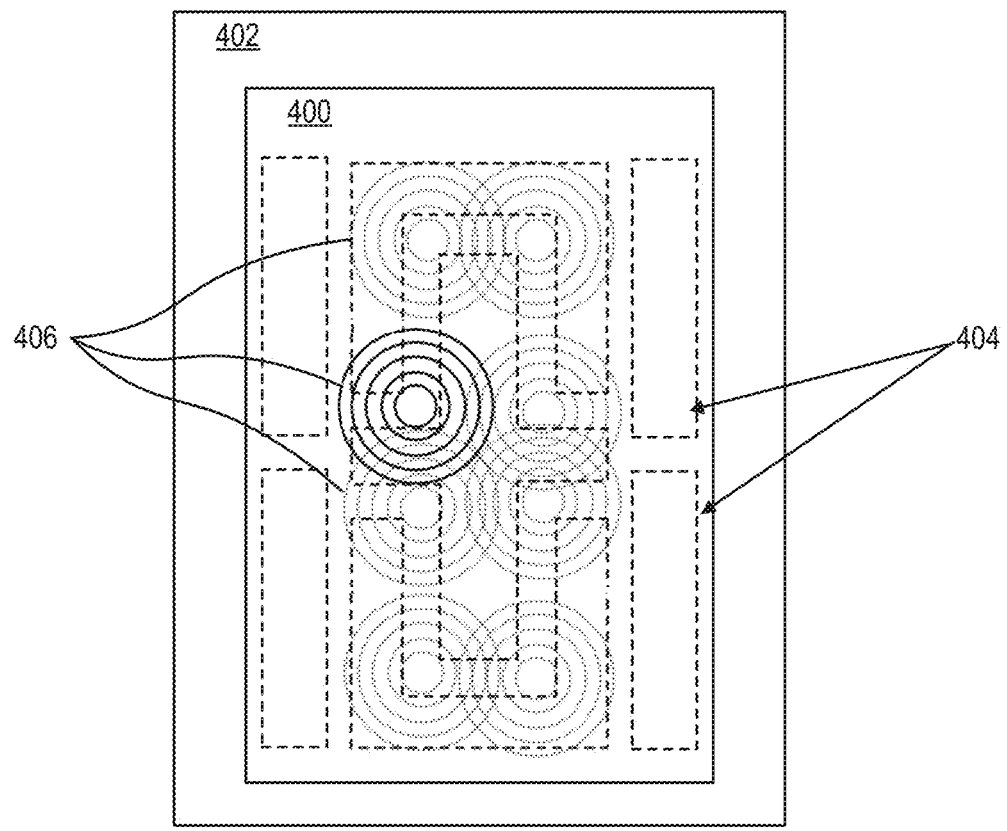
FIG. 4 is a partially schematic top view of a pressure-mitigation apparatus illustrating varied pressure distributions for avoiding ischemia for a mobility-impaired patient in accordance with embodiments of the present technology.

FIG. 4 is a partially schematic top view of a pressure-mitigation apparatus 400 illustrating varied pressure distributions for avoiding ischemia for a mobility-impaired patient in accordance with embodiments of the present technology. As discussed above, when a human body is supported by a contact surface 402 for an extended duration, pressure injuries may form in tissue overlaying bony prominences, such as the skin overlaying the sacrum, coccyx, heels, or hips. These bony prominences often represent the location or locations at which the most pressure is applied by the contact surface 402 and, therefore, may be referred to as the "main pressure point(s)" along the surface of the human body. To prevent the formation of pressure injuries, healthy individuals periodically make minor positional adjustments (also known as "micro-adjustments") to shift the location of the main pressure point. However, individuals having impaired mobility often cannot make these micro-adjustments by themselves. Mobility impairment may be due to physical injury (e.g., a traumatic injury or a progressive injury), movement limitations (e.g., within a vehicle, on an aircraft, or in restraints), medical procedures (e.g., those requiring anesthesia), and/or other conditions that limit an individual's natural movement. For these mobility-impaired individuals, the pressure-mitigation apparatus 400 can be used to shift the location of the main pressure point(s) on their behalf. That is, the pressure mitigation apparatus 400 can create moving pressure gradients to avoid sustained, localized vascular compression and enhance tissue perfusion As shown in FIG. 4, the pressure-mitigation apparatus 400 can include a series of chambers 404 (also referred to as "cells") whose pressure can be individually varied. The chambers 404 may be formed by interconnections between a first or bottom layer and a second or top layer of the pressure-mitigation apparatus 400. The top layer may be comprised of a first material (e.g., an air-permeable, non-irritating material) configured for direct contact with a human body, while the bottom layer may be comprised of a second material (e.g., a non-air-permeable, gripping material) configured for direct contact with the contact surface 402 or an attachment apparatus. In these and other embodiments, the top layer and/or the bottom layer can be comprised of more than one material, such as a coated fabric or a stack of interconnected materials.

A pump, such as the pressure device described below with respect to FIG. 11, can be fluidly coupled to each chamber 404 (e.g., via a corresponding inlet valve), while a controller, such as the controller described below with respect to FIG. 11, may control the flow of fluid (e.g., air) generated by the pump into each chamber 404 on an individual basis in accordance with a predetermined pattern. As further described below, the pump and controller can operate the series of chambers 404 in several different ways. In some embodiments, the chambers 404 have a naturally deflated state, and the controller causes the pump to inflate at least one of the chambers 404 to shift the main pressure point along the anatomy of the user. For example, the pump may inflate at least one of the chambers 404 located directly beneath an anatomical region to momentarily apply contact pressure to that anatomical region and relieve the contact pressure on the surrounding anatomical regions adjacent to the deflated chamber(s) 404. In these and other implementations, the controller may cause the pump to inflate two or more chambers 404 adjacent to an anatomical region to create an open space or void beneath the anatomical region to shift the main pressure point at least momentarily away from the anatomical region. In other embodiments, the chambers 404 have a naturally inflated state, and the controller causes the pump to deflate at least one of the chambers 404 to shift the main pressure point along the anatomy of the user. For example, the pump may be configured to deflate at least one of the chambers 404 located directly beneath an anatomical region, thereby forming a void beneath the anatomical region to momentarily relieve the contact pressure on the anatomical region. Whether configured in a naturally deflated state or a naturally inflated state, the continuous or intermittent alteration of the inflation levels of the individual chambers 404 moves the location of the main pressure point across different portions of the human body. As shown in FIG. 4, for example, inflating and/or deflating the chambers 404 creates temporary contact regions 406 that move across the pressure-mitigation apparatus 400 in a predetermined pattern, and thereby change the location of the main pressure point(s) on the human body for finite intervals of time. Thus, the pressure-mitigation apparatus 400 can simulate the micro-adjustments made by mobile individuals to relieve stagnant pressure application caused by the contact surface 402.

As noted above, the series of chambers 404 may be arranged in an anatomy-specific pattern so that when the pressure within one or more individual chambers is altered, the contact pressure on a specific anatomical region of the human body is relieved (e.g., by shifting the main pressure point elsewhere). As shown in FIG. 4, for example, the main pressure point can be moved between eight different locations corresponding to the eight temporary contact regions 406. In some embodiments the main pressure point shifts between these locations in a predictable manner (e.g., in a clockwise or counter-clockwise pattern), while in other embodiments the main pressure point shifts between these locations in an unpredictable manner (e.g., in accordance with a random pattern, a semi-random pattern, and/or detected pressure levels). Those skilled in the art will recognize that the quantity and position of these temporary contact regions 406 may vary based on the arrangement of the series of chambers 404, the anatomical region supported by the pressure-mitigation apparatus 400, the characteristics of the human body supported by the pressure mitigation apparatus 400, and/or the condition of the user (e.g., whether the user is completely immobilized, partially immobilized, etc.).

In some embodiments, the pressure-mitigation apparatus 400 does not include side supports because the condition of the user (also referred to as a "patient") may not benefit from the positioning provided by the side supports. For example, side supports can be omitted when the patient is medically immobilized (e.g., under anesthesia, in a medically induced coma, etc.) and/or physically restrained by the underlying support surface (e.g., rails along the side of a bed, arm rests on the side of a chair) and/or other structures (e.g., physically restraints holding down the patient, casts, etc.).

FIG. 5 is a flow diagram of a process 500 for manufacturing a pressure-mitigation apparatus in accordance with embodiments of the present technology. Initially, an entity (also referred to as a "manufacturer") can acquire a first sheet comprised of a first material (step 501). The first material may be, for example, an air-permeable, non-irritating material that permits the first sheet to maintain direct contact with a human body for an extended period of time (e.g., several hours) without issue. The first material may also be impervious to liquid. In some embodiments, the manufacturer may form perforations in the first sheet. If the first material is impervious to liquid, the perforations allow for the passage of liquid (e.g., sweat) that may cause irritation. If the first material is not impervious to liquid, the perforations allow for the passage of air to facilitate drying of the first material.

The manufacturer can also acquire a second sheet comprised of a second material (step 502). The second material may be, for example, a non-air-permeable, gripping material that can maintain direct contact with either a support surface or an attachment apparatus without issue. The second material may provide some tackiness to prevent slippage. Said another way, the second material may be designed to promote static friction (also referred to as "stiction") between the pressure-mitigation apparatus and the support surface, thereby limiting relative motion of these objects that are in contact with one another. Generally, the second material is impervious to liquid, though the second material is pervious to liquid in some embodiments (e.g., when frequent replacement of the pressure-mitigation apparatus is likely). Much like the first sheet, the manufacturer may form perforations in the second sheet to enable the passage of fluid (e.g., sweat, water, or air).

Then, the manufacturer can create a cavity by forming an interconnection along the periphery of the first and second sheets (step 503). The interconnection can be formed in several different ways. For example, if the first and second sheets are comprised of thermoplastic(s), then the first and second sheets can be welded together through the application of heat along the periphery. As another example, the first and second sheets may be secured to one another using an adhesive. Similarly, the manufacturer can create a geometric pattern of chambers by forming additional interconnections between the first and second sheets (step 504). Generally, the geometric pattern of the chambers is designed based on the internal anatomy (e.g., the muscles, bones, and vasculature) of a specific anatomical region on which pressure is to be relieved by the pressure-mitigation apparatus. For example, some geometric patterns of chambers are suitable for the dorsal side of a human body in a sitting position, while other geometric patterns of chambers are suitable for the dorsal side of the human body in a supine and/or prone position. The pattern of chambers (or the chambers themselves) may also be designed based on one or more characteristics of the individual(s) who are expected to use the pressure-mitigation apparatus, such as size, weight, or physical ailment. For example, different pressure-mitigation apparatuses may be available for neonatal patients, pediatric patients, average adult patients, bariatric patients, or geriatric patients.

In some embodiments, the manufacturer applies a coating the first sheet and/or the second sheet (step 505). For example, the manufacturer may apply a non-slip coating to the second sheet to ensure the pressure-mitigation apparatus can be secured to either the support surface or the attachment apparatus. As another example, the manufacturer may apply an antimicrobial coating to the first sheet and/or the second sheet to provide protection against fungi, mold, and bacteria.

Selected Embodiments of Attachment Apparatuses

An attachment apparatus is a device that securely attaches a pressure-mitigation apparatus (e.g., the pressure-mitigation apparatuses 100, 200, 300, 400 described above with respect to FIGS. 1A-4) to a support surface, such as a mattress, table, recliner, wheelchair, and/or another type of support surface. The attachment apparatus can be secured, either permanently or temporarily, to the support surface, and the pressure-mitigation apparatus can be secured, either permanently or temporarily, to the attachment apparatus. As such, the attachment apparatus can more accurately and effectively secure the pressure-mitigation apparatus in its optimum/proper position in relation to an anatomical region of a human body. Several examples of attachment apparatuses are described below with respect to FIGS. 6-8. Unless otherwise noted, any features described with respect to one embodiment are equally applicable to the other embodiments. Some features have only been described with respect to a single embodiment of the attachment apparatus for the purpose of simplifying the present disclosure.

Figure 6:
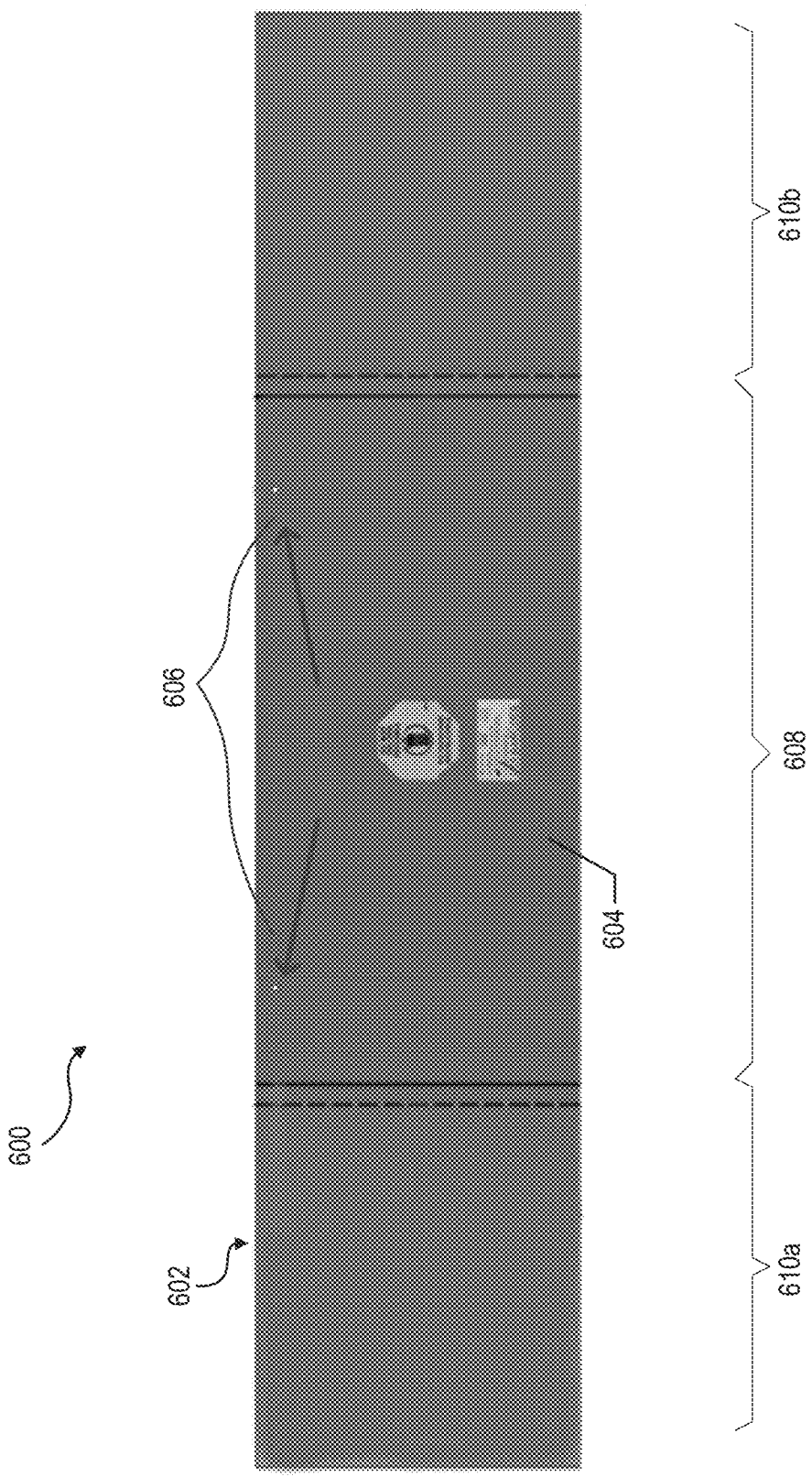
FIG. 6 is a top view of an attachment apparatus for securing a pressure-mitigation apparatus to a support surface in accordance with embodiments of the present technology
Figure 8:
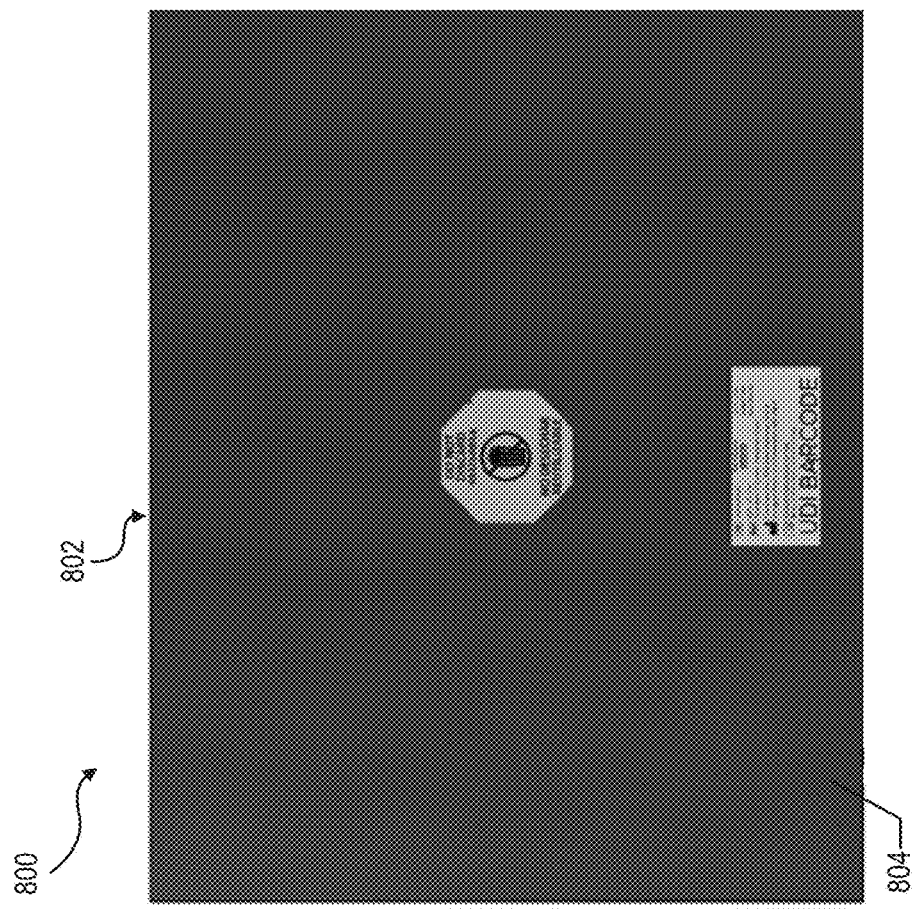
FIG. 8 is a top view of an attachment apparatus for securing a pressure-mitigation apparatus to a support surface in accordance with embodiments of the present technology.

FIG. 6 is a top view of an attachment apparatus 600 (also referred to as an "attachment device" or an "attachment mechanism") for securing a pressure-mitigation apparatus to a support surface in accordance with embodiments of the present technology. The embodiment illustrated in FIG. 6 is generally used to secure pressure-mitigation apparatuses to elongated support surfaces, while the embodiment illustrated in FIG. 8 is generally used to secure pressure-mitigation apparatuses to nonelongated support surfaces. However, all of the attachment apparatuses described herein could be secured to support surfaces of varying lengths, widths, and/or thicknesses. Examples of elongated support surfaces include mattresses, stretchers, operating tables, and procedure tables. Examples of nonelongated support surfaces include chairs (e.g., office chairs, examination chairs, recliners, and wheelchairs) and the seats included in vehicles and airplanes.

The attachment apparatus 600 includes a first portion 602 (also referred to as a "first side") designed to face a support surface and a second portion 604 (also referred to as a "second side") designed to face a pressure-mitigation apparatus. The first portion 602 is arranged opposite the second portion 604, though one or more intermediary layers may be disposed between the first and second portions 602, 604. In some embodiments, the first and second portions 602, 604 represent opposing sides of a component comprised of a single material. For example, the attachment apparatus 600 may be entirely comprised of polyurethane, polypropylene, silicone, or a rubber compound. As another example, the attachment apparatus 600 may be comprised of a sealed, non-porous material to reduce the risk of biohazard contamination and improve infection control. In other embodiments, the first and second portions 602, 604 represent opposing sides of a stack of interconnected materials, such as a core material (e.g., comprised of polyurethane foam, polyethylene foam, latex, wool, cotton, woven fabric(s), non-woven fabric(s), natural fibers, or synthetic fibers), a covering (e.g., comprised of a natural fabric or a synthetic fabric), and/or a coating. For example, the attachment apparatus 600 may include a polyurethane foam core encapsulated by a silicon rubber coating.

In some embodiments, the first portion 602 and/or the second portion 604 can be comprised of at least one adhesive or non-slip material that provides some tackiness. Thus, the first portion 602 and/or the second portion 604 may be designed to promote stiction, thereby limiting relative motion of the pressure-mitigation apparatus in relation to the support surface. For example, a non-slip material that defines an outer surface of the attachment apparatus 600 may include silicone rubber with sufficient tackiness to limit movement of a pressure-mitigation apparatus with respect to a support surface. However, the first and second portions 602, 604 need not be comprised of the same non-slip material(s). For example, the first portion 602 may include a non-slip film, coating, or tape designed to ensure the attachment apparatus 600 is fixedly secured to the support surface, while the second portion 604 may rely on the tackiness provided by silicone rubber to secure the pressure-mitigation apparatus. Accordingly, a pressure-mitigation apparatus may be readily detachable from the attachment apparatus 600. As noted below, however, in some embodiments, the pressure-mitigation apparatus may be permanently secured to the attachment apparatus 600 (e.g., by an adhesive, heat and/or pressure, etc.).

Additionally or alternatively, the attachment apparatus 600 may include one or more openings 606 through which securement components (not shown) can extend to connect the attachment apparatus 600 to the underlying support surface. In the illustrated embodiment, for example, the attachment apparatus 600 includes two openings 606 along its upper periphery that are designed to accept securement components (e.g., hooks, snaps, or tabs) associated with the support surface or the pressure-mitigation device. Other components could be used in addition to, or instead of, the opening(s) 606 to secure the attachment apparatus 600 to the support surface or the pressure-mitigation device. For example, the attachment apparatus 600 may include one or more magnets that are positioned in a predetermined arrangement. In such embodiments, when the attachment apparatus 600 is brought within close proximity of the support surface, magnet(s) may be attracted to magnetically complementary object(s) connected to, or embedded within, the support surface. Similarly, when the attachment apparatus 600 is brought within close proximity of the pressure-mitigation apparatus, magnet(s) may be attracted to magnetically complementary object(s) connected to, or embedded within, the pressure-mitigation apparatus.

Figure 7A:
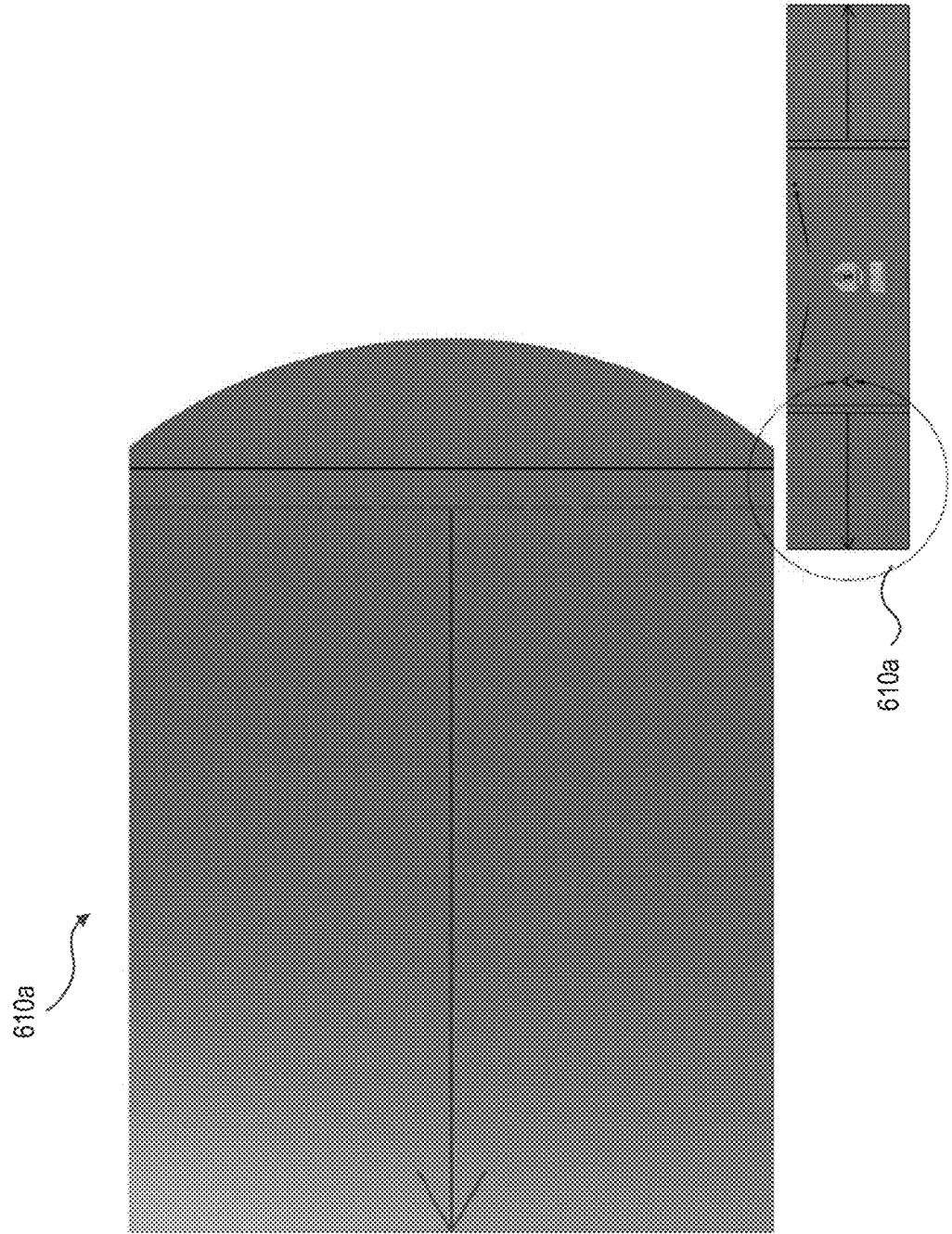
FIG. 7A-7C are top views of a left lateral portion, a central portion, and a right lateral portion, respectively, of the pressure-mitigation apparatus of FIG. 6.
Figure 7B:
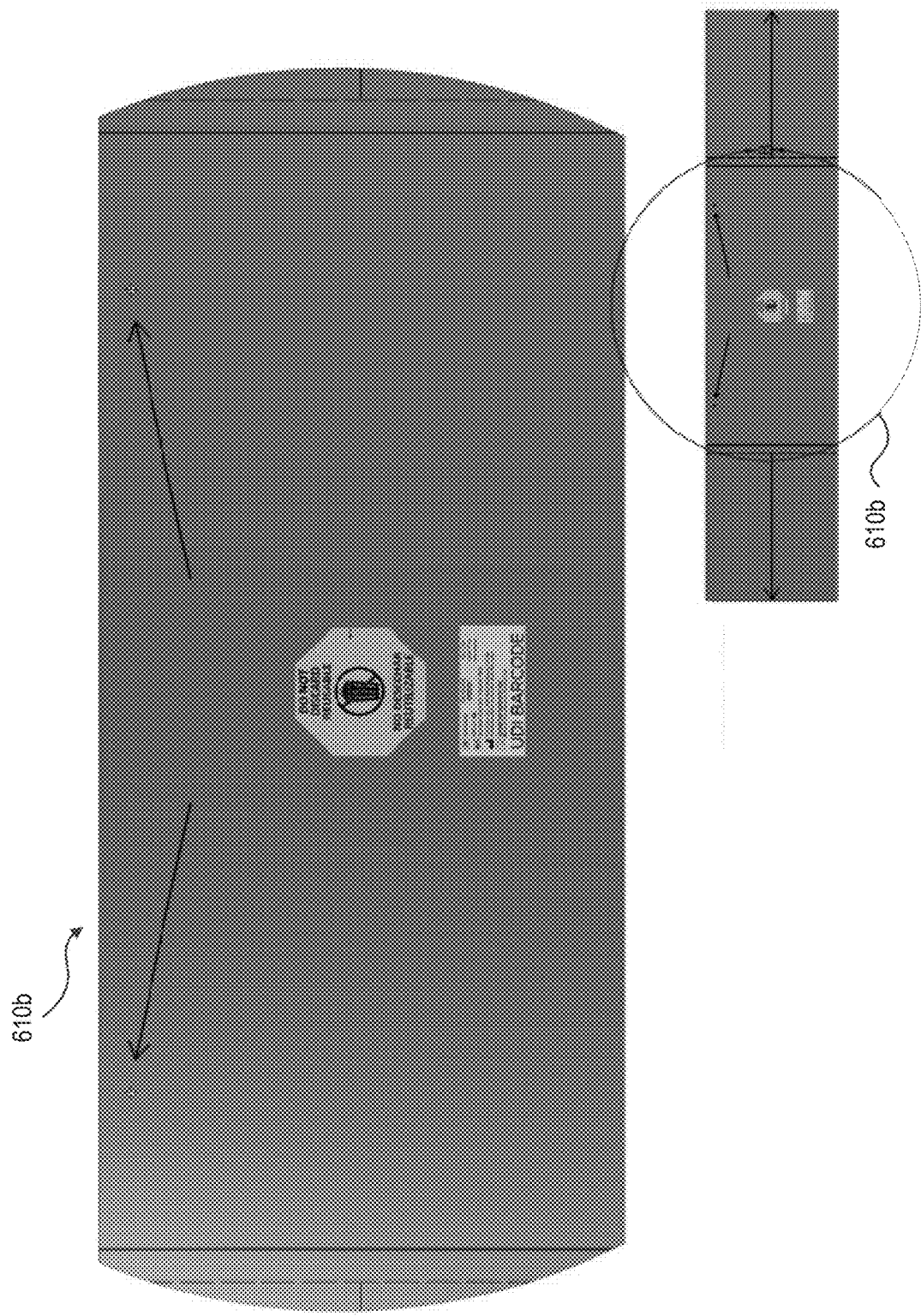
Figure 7C:
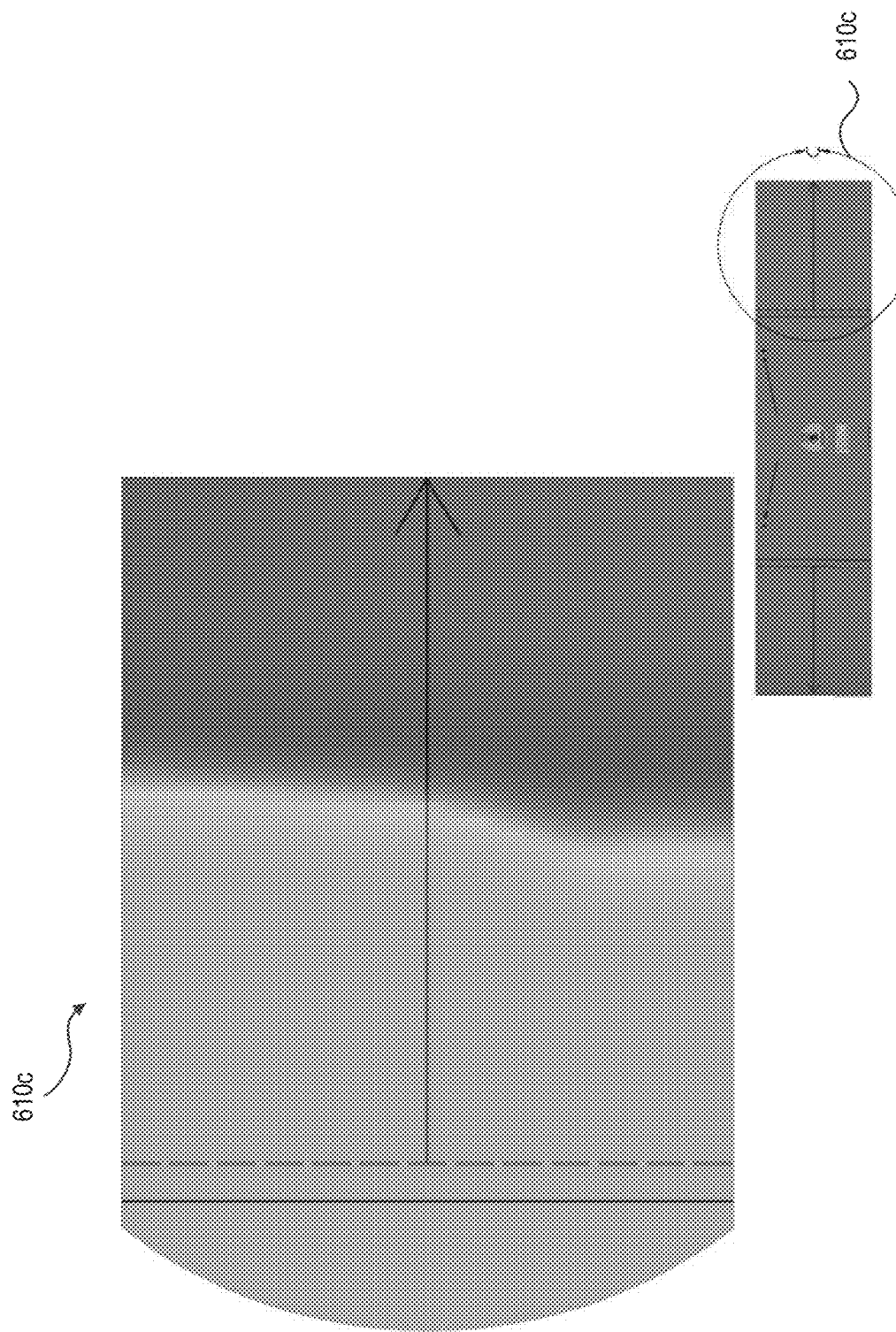

As shown in FIG. 6, the attachment apparatus 600 can include a central portion 608 disposed between opposing lateral portions 610, which may be identified individually as a first lateral portion 610a (also referred to as a "left lateral portion") and a second lateral portion 610b (also referred to as a "right lateral portion"). FIGS. 7A-7C are top views of the left lateral portion 610a, the central portion 608, and the right lateral portion 610b, respectively. To secure the attachment apparatus 600 to a support surface, an individual can wrap the lateral portions 610 at least partially around the support surface. For example, to secure the attachment apparatus 600 to a hospital bed, the lateral portions 610 may be secured along the underside of the hospital bed. In such embodiments, at least part of each lateral portion 610 may be arranged roughly parallel to the central portion 608. As another example, to secure the attachment apparatus 600 to a mattress, the lateral portions 610 may be secured along opposing sides of the mattress. In such embodiments, each lateral portion 610 may be arranged roughly perpendicular to the central portion 608. Some embodiments of the attachment apparatus 600 do not include the lateral portions 610.

FIG. 8 is a top view of an attachment apparatus 800 for securing a pressure-mitigation apparatus to a support surface in accordance with embodiments of the present technology. Similar to the attachment apparatus 600 of FIGS. 6-7C, the attachment apparatus 800 of FIG. 8 includes a first portion 802 (also referred to as a "first side") designed to face the support surface and a second portion 804 (also referred to as a "second side") designed to face the pressure-mitigation apparatus. In some embodiments the first and second portions 802, 804 represent opposing sides of a component comprised of a single material, while in other embodiments the first and second portions 802, 804 represent opposing sides of a stack of at least partially interconnected materials. The first portion 802 and/or the second portion 804 can be comprised of at least one non-slip material to provide some degree of tackiness to at least partially secure the overlying pressure-mitigation apparatus to the underlying support surface.

In contrast to the attachment apparatus 600 of FIG. 6, however, the attachment apparatus 800 of FIG. 8 does not include opposing lateral portions. Instead, the attachment apparatus 800 may be designed such that it can fit entirely within the bounds of the support surface. Such a design may be particularly useful for those support surfaces that have components arranged along their periphery and/or other features that make it difficult to secure or tuck in a lateral portion around the side(s) of the support surface. One example of such a support surface is a wheelchair that has a back portion arranged orthogonal to rear edge of the seat and opposing side features (e.g., clothing guards and/or opposing arms) adjacent to the lateral edges of the seat. In this example, the periphery of the seat (i.e., the support surface) is bounded on three edges, and the attachment apparatus 800 can be laid directly onto the seat of the wheelchair. The attachment apparatus 800 can be used with other seat-like structures, such as recliners, airplane seats, and automobile seats, as well as elongated support surfaces, such as mattresses, stretchers, operating tables, and procedure tables. In some embodiments the attachment apparatus 800 can include connection features, such as snaps, hooks, or holes, that can interface with another component of the support surface to secure the attachment apparatus 800 to the underlying support surface.

The attachment apparatus 600 of FIG. 6 and the attachment apparatus 800 of FIG. 8 can be designed to accommodate pressure-mitigation apparatuses of various widths, lengths, and thicknesses. For example, in various embodiments the attachment apparatus may have a width of 12-18 inches (30.5-45.7 cm), a length of 20-72 inches (50.8-182.9 cm), and a thickness of 0.5-2 inches (1.3-5.1 cm). In these and other embodiments, the attachment apparatus may have a larger or smaller width, length, and/or thickness to accommodate the desired attachment side and pressure-mitigation apparatus attached thereto. Generally, the surfaces of an attachment apparatus will be substantially planar to allow for easier cleaning (e.g., between patients). However, in some embodiments, at least surface of the attachment apparatus may be textured to conform with certain support surfaces (e.g., textured mattresses).

Those skilled in the art will recognize that attachment apparatuses could take forms other than those shown and described with respect to FIGS. 6-8. For example, an attachment apparatus may take the form of an oblong rectangle having a length-to-width ratio of at least two, at least three, or at least five. In such embodiments, an individual could secure multiple attachment apparatuses along the support surface in series of rows or columns. As another example, an attachment apparatus may take the form of a frame having a central opening. In some embodiments the pressure-mitigation apparatus is permitted to contact the support surface through the central opening (e.g., due to the force applied to the pressure-mitigation apparatus by the human body arranged thereon), while in other embodiments the pressure-mitigation apparatus is sufficiently rigid to ensure that a gap remains between the pressure-mitigation apparatus and the support surface.

Figure 9:
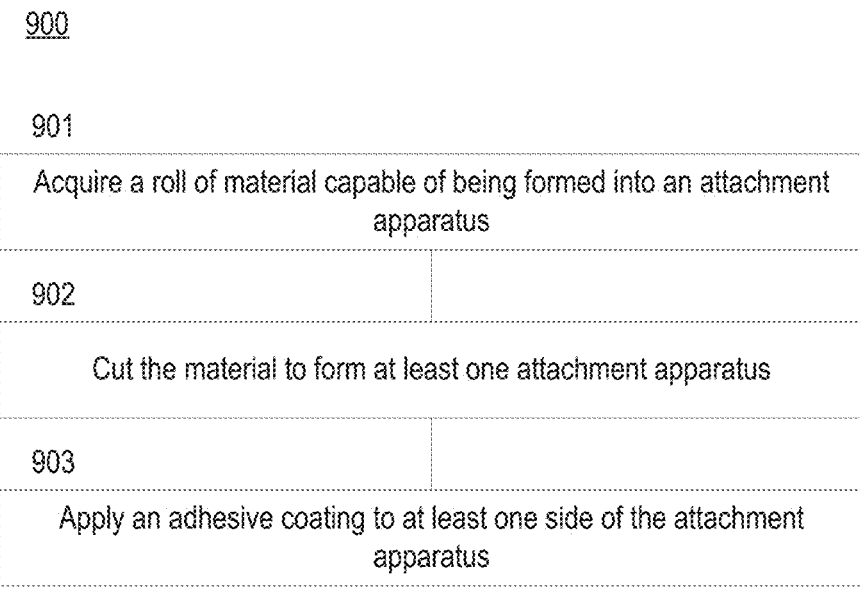
FIG. 9 is a flow diagram of a process for manufacturing an attachment apparatus in accordance with embodiments of the present technology.

FIG. 9 is a flow diagram of a process 900 for manufacturing an attachment apparatus in accordance with embodiments of the present technology. Initially, an entity (also referred to as a "manufacturer") can acquire a roll of material capable of being formed into an attachment apparatus (step 901). The material may be, for example, polyurethane, polypropylene, silicone, or a rubber compound.

Thereafter, the manufacturer can cut the material to form at least one attachment apparatus (step 902). As noted above, the attachment apparatus may take various forms, so the manufacturer may cut the roll of material into multiple rectangular segments, square segments, or elliptical segments.

In some embodiments, the upper surface and/or the lower surface of the attachment apparatus is comprised of a material, such as silicone rubber, with sufficient tackiness to naturally limit movement of the attachment apparatus. In other embodiments, the manufacturer applies an adhesive coating to the upper surface and/or the lower surface of the attachment apparatus (step 903). In such embodiments, the manufacturer may cover the adhesive coating with a cover or a film that must be removed before the attachment apparatus is secured to a support surface, or before a pressure-mitigation apparatus is secured to the attachment apparatus.

Other steps may also be included in some embodiments. For example, some embodiments of attachment apparatuses are comprised of a stack of interconnected materials. Thus, the attachment apparatus may include one or more intermediary layers disposed between a top layer for interfacing with the pressure-mitigation apparatus and a bottom layer for interfacing with the support surface. The intermediary layer(s) may be comprised of polyurethane foam, polyethylene foam, latex, wool, cotton, woven fabric(s), non-woven fabric(s), natural fibers, or synthetic fibers.

Selected Embodiments of Pressure-Mitigation Systems

A pressure-mitigation apparatus may be part of a pressure-mitigation system that also includes an attachment apparatus, a controller device (also referred to as a "controller"), and one or more pumps. The attachment apparatus can ensure the pressure-mitigation apparatus is securely adhered to the support surface. The controller, meanwhile, can cause the pressure on one or more anatomical regions of the human body to be varied by controlling the flow of fluid (e.g., air) produced by the pump(s) into each chamber of the pressure-mitigation apparatus. For example, the controller may controllably inflate one or more chambers, deflate one or more chambers, or any combination thereof.

Figure 10A:
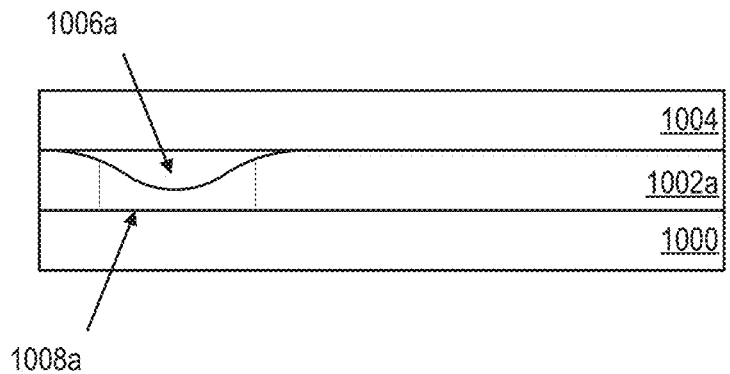
FIG. 10A is a partially schematic side view of a pressure-mitigation apparatus for relieving pressure on a specific anatomical region by chamber deflation in accordance with embodiments of the present technology.

FIG. 10A is a partially schematic side view of a pressure-mitigation apparatus 1002a for relieving pressure on a specific anatomical region by chamber deflation in accordance with embodiments of the present technology. The pressure-mitigation apparatus 1002a can be positioned between a contact surface 1000 (also referred to as a "support surface") and a human body 1004 and, to relieve pressure on a specific anatomical region of the human body 1004, at least one chamber 1008a of a plurality of chambers (referred to collectively as "chambers 1008") proximate to the specific anatomical region at least partially deflates to create an open region or void 1006a beneath the specific anatomical region. In such embodiments, the remaining chambers 1008 may remain inflated. Thus, the pressure-mitigation apparatus 1002a may sequentially deflate chambers 1008 (or arrangements of multiple chambers) to relieve the contact pressure applied to the human body 1004 by the contact surface 1000.

Figure 10B:
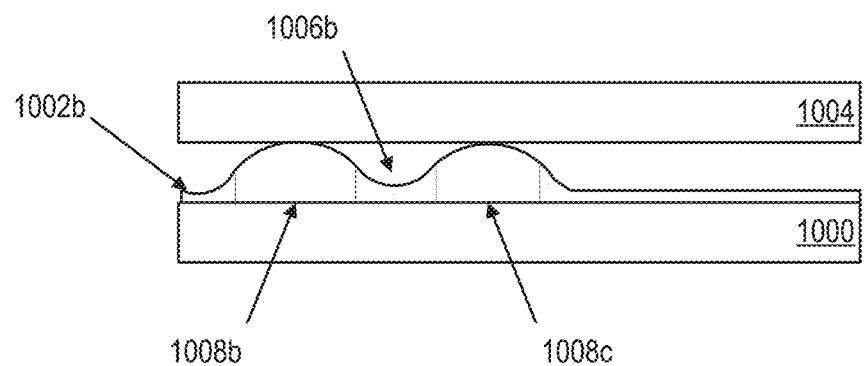
FIG. 10B is a partially schematic side view of a pressure-mitigation apparatus for relieving pressure on a specific anatomical by chamber inflation in accordance with embodiments of the present technology.

FIG. 10B is a partially schematic side view of a pressure-mitigation apparatus 1002b for relieving pressure on a specific anatomical by chamber inflation in accordance with embodiments of the present technology. For example, to relieve pressure at a specific anatomical region of the human body 1004, the pressure-mitigation apparatus 1002b can inflate two chambers 1008b and 1008c disposed directly adjacent to the specific anatomical region to create a void 1006b beneath the specific anatomical region. In such embodiments, the remaining chambers may remain at least partially deflated. Thus, the pressure-mitigation apparatus 1002b may sequentially inflate a chamber (or arrangements of multiple chambers) to relieve the contact pressure applied to the human body 1004 by the contact surface 1000.

The pressure-mitigation apparatuses 1002a, 1002b of FIGS. 10A and 10B are shown to be in direct contact with the contact surface 1000. However, in some embodiments, an attachment apparatus is positioned between the pressure-mitigation apparatuses 1002a, 1002b and the contact surface 1000.

In some embodiments, the pressure-mitigation apparatuses 1002a, 1002b of FIGS. 10A and 10B can have the same configuration of chambers 1008, and the pressure-mitigation apparatuses 1002a, 1002b can operate in both a normally inflated state (described with respect to FIG. 10A) and a normally deflated state (described with respect to FIG. 10B) based on a selection made by an operator (e.g., a medical professional or the user). For example, the operator can use a controller to select a normally deflated mode such that the pressure-mitigation device operates as described with respect to FIG. 10A, and then change the mode of operation to a normally inflated mode such that the pressure-mitigation device operates as described with respect to FIG. 10B. Thus, the pressure-mitigation apparatuses disclosed herein can shift the location of the main pressure point by controllably inflating chambers, controllably deflating chambers, or a combination thereof.

Figure 11:
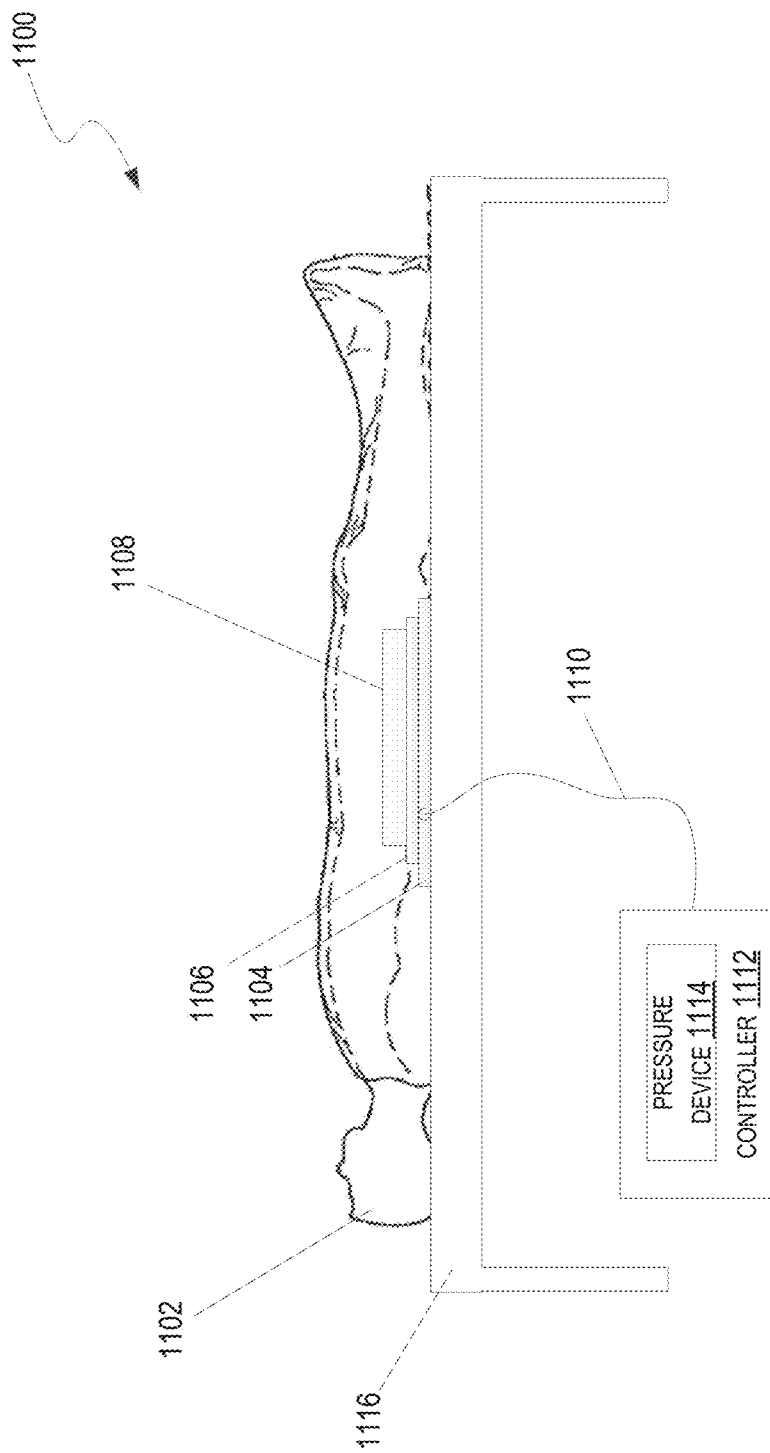
FIG. 11 includes a side view of a pressure-mitigation system configured in accordance with embodiments of the present technology.

FIG. 11 includes a side view of a pressure-mitigation system 1100 (also referred to as "the system 1100") for orienting an individual 1102 over a pressure-mitigation apparatus 1106 in accordance with embodiments of the present technology. The system 1100 can include a pressure-mitigation apparatus 1106 that include side supports 1108, an attachment apparatus 1104, a pressure device 1114, and a controller 1112. The attachment apparatus 1104 may be responsible for securing the pressure-mitigation apparatus 1106 to the support surface 1116. Further examples of the pressure-mitigation apparatus are discussed in detail with respect to FIGS. 1-3, and further examples of the attachment apparatus are discussed in detail with respect to FIGS. 6-8.

In this embodiment, the pressure-mitigation apparatus 1106 includes a pair of elevated side supports 1108 that extend longitudinally along opposing sides of the pressure-mitigation apparatus 1106. The pressure-mitigation apparatus 1106 includes a series of chambers interconnected on a base material. As further described above, the chambers may be arranged in a geometric pattern designed to mitigate the pressure applied to a specific anatomical region by the support surface 1116.

The elevated side supports 1108 can be configured to actively orient the specific anatomical region of the individual 1102 over the series of chambers. For example, the elevated side supports 1108 may be responsible for actively orienting the specific anatomical region widthwise over the epicenter of the geometric pattern. The specific anatomical region may be the sacral region, scapular region, or the cephalic/cranial region. However, the specific anatomical region could be any region of the body that is susceptible to pressure, and thus the formation of pressure ulcers. The elevated side supports 1108 may be configured to be ergonomically comfortable. For example, the elevated side supports 1108 may include a recess designed to accommodate the forearm, which permits pressure to be offloaded from the elbow.

The elevated side supports 1108 may be significantly larger in size than the chambers of the pressure-mitigation apparatus 1106. Accordingly, the elevated side supports 1108 may create a barrier that restricts lateral movement of the individual 1102. In some embodiments, the elevated side supports 1108 are approximately 2 inches, 3 inches, 4 inches, or 6 inches taller in height as compared to the average height of an inflated chamber. Because the elevated side supports 1106 straddle the individual 1102, the elevated side supports 1108 can act as barriers for maintaining the position of the individual 1102 on top of the pressure-mitigation apparatus 1106.

In some embodiments, the inner side walls of the elevated side supports 1108 form, following inflation, a firm surface at a steep angle of orientation with respect to the pressure-mitigation apparatus 1106. For example, the inner side walls may be on a plane of approximately 115 degrees, plus or minus 24 degrees, from the substantially horizontal plane defined by the upper surface of the pressure-mitigation apparatus 1106. These steep inner side walls can form a channel that naturally positions the individual 1102 over the chambers of the pressure-mitigation apparatus 1106. Thus, inflation of the elevated side supports 1108 may actively force the individual 1102 into the appropriate position for mitigating pressure by orienting the individual 1102 in the correct location with respect to the chambers of the pressure-mitigation apparatus 1106.

After the initial inflation cycle has been completed, the pressure of each elevated side support 1108 may be lessened to increase comfort and prevent excessive force against the lateral sides of the individual 1102. Oftentimes a medical professional (e.g., a physician, nurse, or caregiver) will be present during the initial inflation cycle to ensure the elevated side supports 1108 properly position the individual 1102 over the pressure-mitigation apparatus 1106.

The controller 1112 can be configured to regulate the pressure of each chamber included in the pressure-mitigation apparatus 1106 and/or each elevated side support 1108 via a pressure device 1114 (e.g., an air pump) and multi-channel tubing 1110. For example, the chambers may be controlled in a specific pattern to preserve blood flow and reduce pressure applied to the individual 1102 when inflated (pressurized) and deflated (depressurized) in a coordinated fashion by the controller 1112. In some embodiments, the multi-channel tubing 1110 is connected between the pressure-mitigation apparatus 1106 and the pressure device 1114. Accordingly, the pressure-mitigation apparatus 1106 may be fluidly coupled to a first end of the multi-channel tubing 1110, and the pressure device 1114 may be fluidly coupled to a second end of the multi-channel tubing 1110. In other embodiments, a first segment of the multi-channel tubing 1110 is connected between the pressure device 1114 and the controller 1112 and a second segment of the multi-channel tubing 1110 is connected between the controller 1112 and the pressure-mitigation apparatus 1106. In such embodiments, the pressure device 1114 and the pressure-mitigation apparatus 1106 can be fluidly connected to one another via the controller 1112.

As noted above, high-acuity patients are often admitted to hospitals to treat conditions that impact mobility, such as strokes and acute kidney injuries. However, impaired mobile can lead to vascular compression in certain anatomical regions of the human body, and the vascular compression can lead to ischemia-reperfusion injuries (also referred to as "ischemic injuries" or "reperfusion injuries"). To prevent or address ischemia-reperfusion injuries, a pressure-mitigation apparatus may be positioned between a human body and a support surface that applies pressure on certain anatomical region(s) of the human body.

FIG. 12 is a flow diagram of a process 1200 for deploying a pressure-mitigation system designed to prevent and/or address ischemia-reperfusion injuries in accordance with embodiments of the present technology. Initially, an individual can acquire a pressure-mitigation apparatus to be placed between a human body and a support surface (step 1201). The individual may be the person who will be treated by the pressure-mitigation system or some other person (e.g., a physician, nurse, or caregiver). In some embodiments, the individual selects the pressure-mitigation apparatus from amongst multiple pressure-mitigation apparatuses designed for different body types, anatomical regions, or support surfaces.

The individual can also acquire an attachment apparatus associated with the pressure-mitigation apparatus and/or the support surface (step 1202). For example, if the pressure-mitigation apparatus is designed for human bodies in the prone position, then the individual may acquire an attachment apparatus designed for an elongated support surface. As another example, if the pressure-mitigation apparatus is designed for human bodies in the sitting position, then the individual may acquire an attachment apparatus designed for a nonelongated support surface.

The individual can then secure the lower surface of the attachment apparatus to the support surface (step 1203). As noted above, the attachment apparatus can be comprised of at least one material that provides some tackiness. In some embodiments, the lower surface of the attachment apparatus is comprised of a material, such as silicone rubber, with sufficient tackiness to naturally limit movement. In some embodiments, the lower surface of the attachment apparatus includes an adhesive film with sufficient tackiness to limit movement through more permanent adhesion. In such embodiments, the individual may need to remove a cover or a film from the bottom surface of the attachment apparatus before securing the attachment apparatus to the support surface. In some embodiments, the attachment apparatus includes one or more design features, such as perforations or notches, through which securement components can extend. Examples of securement components include hooks, snaps, tabs, and other structural features.

The individual can then secure the pressure-mitigation apparatus to the upper surface of the attachment apparatus (step 1204). In some embodiments, the upper surface of the attachment apparatus and/or the lower surface of the pressure-mitigation apparatus is comprised of a material, such as silicone rubber, with sufficient tackiness to naturally limit movement. In some embodiments, the upper surface of the attachment apparatus and/or the lower surface of the pressure-mitigation apparatus includes an adhesive film with sufficient tackiness to limit movement through more permanent adhesion. In such embodiments, the individual may need to remove a cover or a film from the upper surface of the attachment apparatus and/or the lower surface of the pressure-mitigation apparatus before securing the pressure-mitigation apparatus to the attachment apparatus. In some embodiments, the attachment apparatus and/or the pressure-mitigation apparatus includes one or more design features, such as perforations or notches, through which securement components can extend. For example, a protruding feature accessible along the support surface may extend through a perforation through the attachment apparatus and a perforation through the pressure-mitigation apparatus.

The individual can then connect the pressure-mitigation apparatus to a controller (step 1205). For example, as shown in FIG. 11, the individual may fluidly couple the controller to the pressure-mitigation apparatus using multi-channel tubing. In some embodiments, the controller may be configured to automatically determine whether a pressure-mitigation apparatus has been connected. For example, by monitoring the connection between a fluid interface accessible along the exterior surface of the controller and the pressure-mitigation apparatus, the controller can detect which type of pressure-mitigation apparatus has been connected.

Thereafter, the human body to be treated using the pressure-mitigation system can be arranged over the pressure-mitigation apparatus (step 1206). The pressure-mitigation apparatus may include a geometric pattern of chambers designed to mitigate the pressure on a specific anatomical region of the human body. Accordingly, the human body may need to be oriented over a particular region (also referred to as a "target region") of the pressure-mitigation apparatus. As shown in FIGS. 1A-2B, the target region may be visually distinguishable along the upper surface of the pressure-mitigation apparatus.

The controller can then cause the chambers of the pressure-mitigation apparatus to be inflated in accordance with a pattern (step 1207). More specifically, the controller can cause the pressure on anatomical region(s) of the human body to be varied by controllably inflating chamber(s), deflating chamber(s), or any combination thereof. The pattern may correspond to the pressure-mitigation apparatus. For example, upon detecting that a given pressure-mitigation apparatus has been connected to the controller, the controller may examine a library of patterns corresponding to different pressure-mitigation apparatuses having different counts/arrangements of chambers to identify the appropriate pattern.

Unless contrary to physical possibility, it is envisioned that the steps described above may be performed in various sequences and combinations. For example, the individual may secure the pressure-mitigation apparatus to the attachment apparatus before securing the attachment apparatus to the support surface. Other steps may also be included in some embodiments. For example, before causing the chambers of the pressure-mitigation apparatus to be inflated in accordance with the pattern, the controller may prompt an operator to specify a characteristic of the human body to be treated by the pressure-mitigation system, such as the size, weight, degree of immobility, or position.

Processing System

Figure 13:
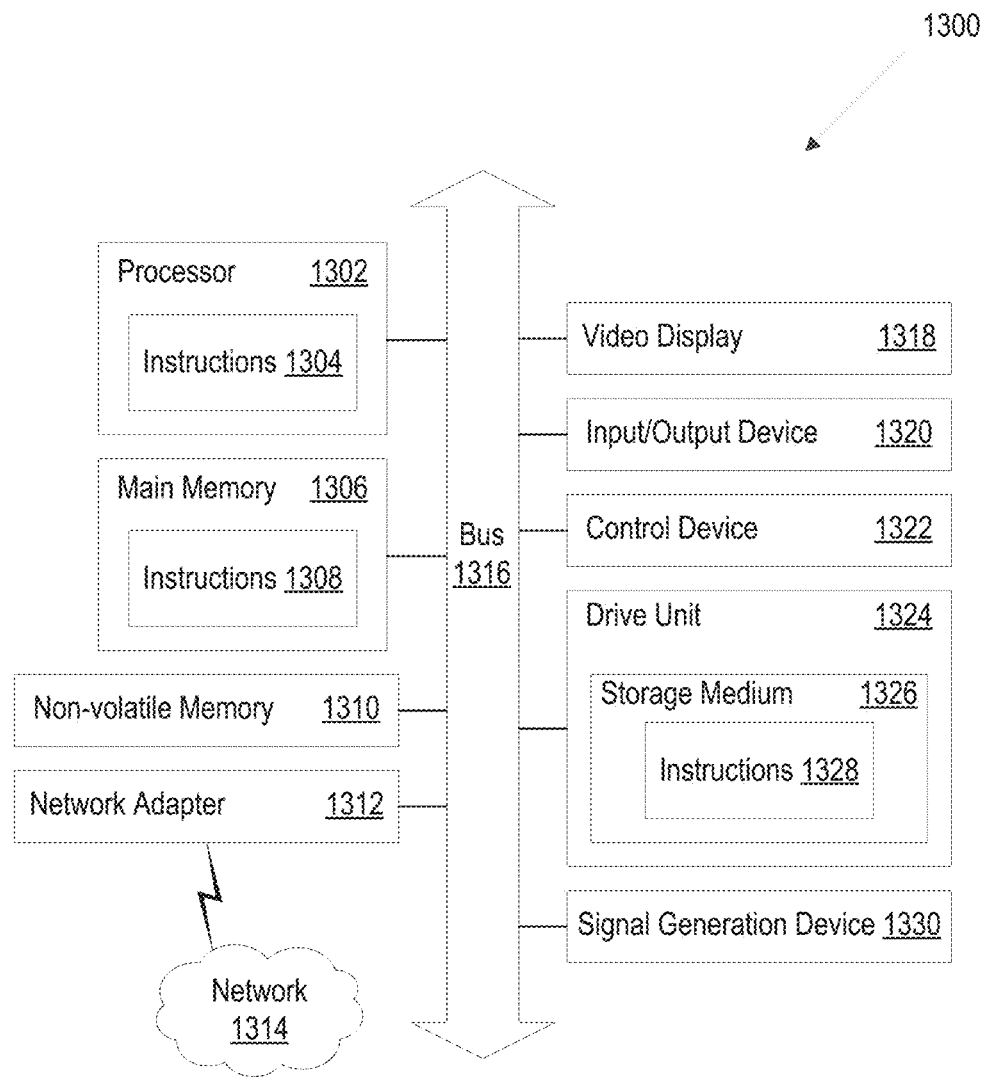
FIG. 13 is a block diagram illustrating an example of a processing system in which at least some operations described herein can be implemented.

FIG. 13 is a block diagram illustrating an example of a processing system 1300 in which at least some operations described herein can be implemented. For example, some components of the processing system 1300 may be hosted on a controller (e.g., controller 1112 of FIG. 11) responsible for controlling a pressure-mitigation apparatus (e.g., pressure-mitigation apparatus 1106 of FIG. 11).

The processing system 1300 may include one or more central processing units ("processors") 1302, main memory 1306, non-volatile memory 1310, network adapter 1312 (e.g., network interface), video display 1318, input/output devices 1320, control device 1322 (e.g., keyboard and pointing devices), drive unit 1324 including a storage medium 1326, and signal generation device 1330 that are communicatively connected to a bus 1316. The bus 1316 is illustrated as an abstraction that represents one or more physical buses and/or point-to-point connections that are connected by appropriate bridges, adapters, or controllers. The bus 1316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1300 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1300.

While the main memory 1306, non-volatile memory 1310, and storage medium 1326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1328. The term "machine-readable medium" and "storage medium" shall also be taken to include any medium that is capable of storing, encoding, or carrying a set of instructions for execution by the processing system 1300.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1304, 1308, 1328) set at various times in various memory and storage devices in a computing device. When read and executed by the one or more processors 1302, the instruction(s) cause the processing system 1300 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1310, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1312 enables the processing system 1300 to mediate data in a network 1314 with an entity that is external to the processing system 1300 through any communication protocol supported by the processing system 1300 and the external entity. The network adapter 1312 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1312 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

EXAMPLES

Several aspects of the present technology are set forth in the following examples.
1. A system comprising:
    a pressure-mitigation apparatus that includes a geometric arrangement of inflatable chambers formed by interconnections between a top layer and a bottom layer, wherein the inflatable chambers are configured to mitigate contact pressure applied to a human body by a support surface when pressure in the inflatable chambers is varied; and
    an attachment apparatus for securing the pressure-mitigation apparatus to the support surface.
2. The system of example 1
    wherein the top layer is comprised of a first material configured for direct contact with the human body, and
    wherein the bottom layer is comprised of a second material configured for direct contact with the attachment apparatus.
3. The system of example 1 wherein the attachment apparatus is comprised of a material that provides sufficient tackiness to naturally limit movement of the pressure-mitigation apparatus in relation to the support surface.
4. The system of example 3 wherein the material is polyurethane, polypropylene, silicone, or a rubber compound.
5. The system of example 1 wherein the attachment apparatus includes a first adhesive film disposed along a top surface that contacts the bottom layer of the pressure-mitigation apparatus.
6. The system of example 5 wherein the attachment apparatus includes a second adhesive film disposed along a bottom surface that contacts the support surface.
7. The system of example 1 wherein the attachment apparatus includes
    a top layer that contacts the bottom layer of the pressure-mitigation apparatus, and
    a bottom layer that contacts the support surface.
8. The system of example 7 wherein the attachment apparatus further includes a pliable core disposed between the top and bottom layers.
9. The system of example 8 wherein the pliable core is comprised of polyurethane foam, polyethylene foam, latex, wool, cotton, a woven fabric, a non-woven fabric, natural fibers, or synthetic fibers.
10. A method for manufacturing a pressure-mitigation apparatus designed to mitigate pressure applied to a human body by a support surface, the method comprising:
    acquiring a first sheet comprised of a first material;
    acquiring a second sheet comprised of a second material;
    creating a cavity by forming an interconnection along a periphery of the first and second sheets; and
    creating a geometric pattern of chambers by forming at least one additional interconnection between the first and second sheets,
        wherein the chambers are formed such that each chamber can be independently pressurized.
11. The method of example 10 wherein the first material is liquid-impervious material configured for direct contact with a human body.
12. The method of example 10 further comprising:
    forming perforations in the first sheet to allow the passage of fluids through the first sheet into the cavity.
13. The method of example 12 further comprising:
    securing a liquid-impervious lining to an interior surface of the first sheet to inhibit the fluids from entering the chambers.
14. The method of example 10 wherein the second material is a liquid-impervious material configured for direct contact with a support surface or an attachment apparatus
15. The method of example 10 further comprising:
    applying an antimicrobial coating to an exterior surface of the first sheet, the second sheet, or any combination thereof.
16. The method of example 10 further comprising:
    applying a non-slip coating to an exterior surface of the first sheet, the second sheet, or any combination thereof.
17. A method for manufacturing an attachment apparatus designed to secure a pressure-mitigation apparatus to a support surface, the method comprising:
    acquire a roll of pliable material that provides sufficient tackiness to naturally limit movement of the pressure-mitigation apparatus in relation to the support surface;
    cutting the pliable material into a first segment and a second segment;
    creating a cavity by forming an interconnection along a periphery of the first and second segments; and
    inserting a pliable core into the cavity.
18. The method of example 17 further comprising:
    applying an adhesive coating to an exterior surface of the first segment, the second segment, or any combination thereof
19. The method of example 17 further comprising:
    forming perforations in the first segment to allow the passage of fluids into the cavity.
20. The method of example 17 wherein the pliable core is comprised of polyurethane foam, polyethylene foam, latex, wool, cotton, a woven fabric, a non-woven fabric, natural fibers, or synthetic fibers.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for manufacturing an attachment apparatus designed to secure, to a support surface, a pressure-mitigation apparatus, that includes a plurality of chambers that individually are controlled to vary pressure therein, the method comprising:
   acquire a roll of pliable material that provides tackiness to naturally limit movement of the pressure-mitigation apparatus in relation to the support surface;
   cutting the pliable material into a first segment and a second segment;
   creating a cavity by forming an interconnection along a periphery of the first and second segments; and
   inserting a pliable core into the cavity.

2. The method of claim 1 further comprising:
   applying an adhesive coating to an exterior surface of the first segment, the second segment, or any combination thereof.

3. The method of claim 1 further comprising:
   forming perforations in the first segment to allow the passage of fluids into the cavity.

4. The method of claim 1 wherein the pliable core is comprised of polyurethane foam, polyethylene foam, latex, wool, cotton, a woven fabric, a non-woven fabric, natural fibers, or synthetic fibers.

5. The method of claim 1 wherein the pliable material is comprised of silicone rubber.

6. The method of claim 2 further comprising:
   applying a film to the adhesive coating to preserve adhesiveness until the attachment apparatus is to be situated between the pressure-mitigation apparatus and the support surface.

7. The method of claim 1 further comprising:
   applying an adhesive tape to an exterior surface of the first segment, so as to ensure that the attachment apparatus is fixedly securable to the support surface.

8. The method of claim 7 wherein the second segment relies on the tackiness provided by the pliable material, such that the pressure-mitigation apparatus is readily detachable from the attachment apparatus.

9. The method of claim 1 further comprising:
   forming, in the first and second segments, one or more openings through which securement components are able to extend to connect the attachment apparatus to the support surface.

10. The method of claim 9 wherein the securement components are associated with the support surface, and wherein a position in which each opening is formed is based on a location of a corresponding securement component along the support surface.

11. The method of claim 1 further comprising:
    positioning, in the cavity, one or more magnets in a predetermined arrangement.

12. The method of claim 11 wherein the predetermined arrangement allows the attachment apparatus to be connected to magnetically complementary objects that are connected to, or embedded within, the support surface.

13. The method of claim 11 wherein the predetermined arrangement allows the attachment apparatus to be connected to magnetically complementary objects that are connected to, or embedded within, the pressure-mitigation apparatus.

* * * * *